US012583848B2

(12) United States Patent
Makarov et al.

(10) Patent No.: US 12,583,848 B2
(45) Date of Patent: Mar. 24, 2026

(54) ISOXAZOLE-3-CARBOXAMIDE DERIVATIVES AND THEIR USE FOR TREATMENT OF DISEASES CAUSED BY VIRUS INFECTION

(71) Applicants: Collaborations Pharmaceuticals, Inc., Raleigh, NC (US); Universitätsklinikum Jena, Jena (DE)

(72) Inventors: Vadim Makarov, Moscow (RU); Michaela Schmidtke, Jena (DE); Sean Ekins, Fuquay Varina, NC (US)

(73) Assignees: Collaborations Pharmaceuticals, Inc.; Universitätsklinikum Jena, Jena (DE)

( * ) Notice: Subject to any disclaimer, the term of this patent is extended or adjusted under 35 U.S.C. 154(b) by 888 days.

(21) Appl. No.: 17/763,932

(22) PCT Filed: Sep. 25, 2020

(86) PCT No.: PCT/US2020/052773
§ 371 (c)(1),
(2) Date: Mar. 25, 2022

(87) PCT Pub. No.: WO2021/062189
PCT Pub. Date: Apr. 1, 2021

(65) Prior Publication Data

US 2022/0298149 A1 Sep. 22, 2022

Related U.S. Application Data

(60) Provisional application No. 62/950,546, filed on Dec. 19, 2019, provisional application No. 62/907,231, filed on Sep. 27, 2019.

(51) Int. Cl.
*C07D 413/12* (2006.01)
*A61K 45/06* (2006.01)
*A61P 31/16* (2006.01)

(52) U.S. Cl.
CPC ............ *C07D 413/12* (2013.01); *A61K 45/06* (2013.01); *A61P 31/16* (2018.01)

(58) Field of Classification Search
CPC .. C07D 413/12; A61K 45/06; A61K 31/4245; A61P 31/16
See application file for complete search history.

(56) References Cited

U.S. PATENT DOCUMENTS

| | | | | |
|---|---|---|---|---|
| 5,464,848 | A * | 11/1995 | Diana ..................... | A61P 31/12 548/131 |
| 11,696,914 | B1 | 7/2023 | Ekins et al. | |
| 2011/0065764 | A1 | 3/2011 | Roughton et al. | |
| 2012/0095002 | A1 | 4/2012 | Ratcliffe et al. | |
| 2019/0054068 | A1 | 2/2019 | Griffioen et al. | |

FOREIGN PATENT DOCUMENTS

| | | | |
|---|---|---|---|
| EP | 4025212 | B1 | 2/2025 |

OTHER PUBLICATIONS

Basha, et al.; International Journal of Drug Discovery and Technology, v1, pp. 91-96 (2010). (Year: 2010).*
Ali, et al.; Journal of the Chemical Society of Pakistan, v36, pp. 150-169; 2014 (Year: 2014).*
Basha, et al.; BMC Research Notes, v5, Article 105, pp. 1-7; 2012 (Year: 2012).*
Galabov, et al.; Pril (Makeon Akad Nauk, Umet Odd Nauki), v36, pp. 91-99; 2015 (Year: 2015).*
Patani, G. A., LaVoie, E. J.; Chemical Reviews, v96, pp. 3147-3176; 1996 (Year: 1996).*
Schmidtke, et al.; Antiviral Research, v81, pp. 56-63; 2009 (Year: 2009).*
Brown, Bioisosteres in Medicinal Chemistry,Wiley-VCH, 2012 (Year: 2012).*
Egorova, et al.; European Journal of Medicinal Chemistry, v188, Article 112007, pp. 1-16; 2020 (Year: 2020).*
Chen et al. (2001) "[alpha]Gal-conjugated anti-rhinovirus agents: chemo-enzymatic syntheses and testing of anti-Gal binding," Royal Chemical Society Journal, Perkin Transactions 1, No. 14, pp. 1716-1722.
Extended European Search Report corresponding to European Application No. 20867155.2-1110 dated Jul. 21, 2023.
Makarov et al. (2005) "Novel [(biphenyloxy)propyl]isoxazole derivatives for inhibition of human rhinovirus 2 and coxsackievirus B3 replication," Journal of Antimicrobial Chemotherapy, vol. 55, No. 4, pp. 483-488.
Schmidtke et al. (2009) "New pleconaril and [(biphenyloxy)propyl]isoxazole derivatives with substitutions in the central ring exhibit antiviral activity against pleconaril-resistant coxsackievirus B3," Antiviral Research, vol. 81, No. 1, pp. 56-63.
Supplementary European Search Report corresponding to European Application No. 20867155.2-1110 dated Aug. 8, 2023.
"Aviragen Antiviral Drug Vapendavir Fails Phase IIb Study in Asthma Patients." (2017).
"Aviragen Therapeutics Announces Top-Line Results from Phase 2b SPIRITUS Trial of Vapendavir." (2017).
"Effects of Pleconaril Nasal Spray on Common Cold Symptoms and Asthma Exacerbations Following Rhinovirus Exposure (Study P04295)." (2018). Available from: clinicaltrials.gov/ct2/show/NCT00394914.
Abzug et al., "Double blind placebo-controlled trial of pleconaril in infants with enterovirus meningitis." Pediatr. Infect. Dis. J., vol. 22(4), pp. 335-340 (2003).
Aradottir et al., "Severe neonatal enteroviral hepatitis treated with pleconaril." Pediatr. Infect. Dis. J., vol. 20, pp. 457-459 (2001).

(Continued)

*Primary Examiner* — Jeffrey S Lundgren
*Assistant Examiner* — W. Justin Youngblood
(74) *Attorney, Agent, or Firm* — Jenkins, Taylor & Hunt, P.A.

(57) ABSTRACT

Isoxazole-3-carboxamide derivatives and their use in treating viral infections and diseases, such as diseases caused by viruses of the Picornaviridae family of viruses (e.g., rhinoviruses, enteroviruses, and coxsackieviruses) is described. The derivatives have good efficacy against a range of viruses, including pleconaril-resistant viral strains, and have low induction of cytochrome P4503A4 (CYP3A4).

20 Claims, 13 Drawing Sheets

(56) References Cited

OTHER PUBLICATIONS

Braun et al., "Molecular mechanism of a specific capsid binder resistance caused by mutations outside the binding pocket." Antiviral Res., vol. 123, pp. 138-145 (2015).
Caliguiri et al., "Effect of arildone on modifications of poliovirus in vitro." Virology, vol. 105(1), pp. 86-93 (1980).
Corne et al., "Frequency, severity, and duration of rhinovirus infections in asthmatic and non-asthmatic individuals: a longitudinal cohort study." Lancet, vol. 359, pp. 831-834 (2002).
De Palma et al., "Selective inhibitors of picornavirus replication." J. Med. Res. Rew., vol. 28, pp. 823-884 (2008).
DeMuri et al., "Clinical Features, Virus Identification, and Sinusitis as a Complication of Upper Respiratory Tract Illness in Children Ages 4-7 Years." J. Pediatr., vol. 171, pp. 133-139.e1 (2016).
Diana et al., "Antiviral activity of some .beta.-diketones. 3. Aryl bis(.beta.-diketones). Antiherpetic activity." J. Med. Chem., vol. 21, pp. 689-692 (1978).
Diana et al., "Antiviral activity of some .beta.-diketones. 4. Benzyl diketones. In vitro activity against both RNA and DNA viruses." J. Med. Chem., vol. 21, pp. 889-894 (1978).
Diana et al., "Antiviral activity of some .beta.-diketones. 1. Aryl alkyl diketones. In vitro activity against both RNA and DNA viruses." Med. Chem., vol. 20, pp. 750-756 (1977).
Diana et al., "Antiviral activity of some .beta.-diketones. 2. Aryloxy alkyl diketones. In vitro activity against both RNA and DNA viruses." Med. Chem., vol. 20, pp. 757-761 (1977).
Egorova, "Back to the future: Advances in development of broad-spectrum capsid-binding inhibitors of enteroviruses." Eur. J. Med. Chem., vol. 178, pp. 606-622 (2019).
Evans et al., "Development of a respiratory disease model for enterovirus D68 in 4-week-old mice for evaluation of antiviral therapies." Antiviral Res., vol. 162, pp. 61-70 (2019).
Greenwood, "Curing the Common Cold." Scientific American, Jan. 1, 2011 (5 pages) (2011). Available from: https://www.scientificamerican.com/article/curing-the-common-cold.
Hall et al., "The interaction between St John's wort and an oral contraceptive." Clin. Pharmacol. Therap., vol. 74, pp. 525-535 (2003).
Hayden et al., "Efficacy and Safety of Oral Pleconaril for Treatment of Colds Dues to Picornaviruses in Adults: Results of 2 Double-Blind, Ramdonized, Placebo-Controlled Trials." Clin. Infect. Dis., vol. 36, pp. 1523-1532 (2003).
Heinz et al., "Genetic and Molecular Analyses of Spontaneous Mutants of Human Rhinovirus 14 That Are Resistant to an Antiviral Compound." J. Virol., vol. 63, pp. 2476-2485 (1989).
Hsu, Front. Immunol., "Influenza Virus: A Master Tactician in Innate Immune Evasion and Novel Therapeutic Interventions." vol. 9, Article No. 743 (11 pages) (2018).
Hurst et al., "Evaluation of antiviral therapies in respiratory and neurological disease models of Enterovirus D68 infection in mice." Virology, vol. 526, pp. 146-154 (2019).
International Preliminary Report on Patentability Corresponding to International Patent Application No. PCT/US 2020/052773 dated Apr. 7, 2022.
International Search Report and Written Opinion of the International Searching Authority corresponding to International Patent Application No. PCT/US 2020/052773 dated Jan. 4, 2021.
Ivashkiv et al., "Regulation of type I interferon responses." Nat. Rev. Immunol., vol. 14, pp. 36-49 (2014).
Iwasaki et al., "Innate immunity to influenza virus infection." Nat. Rev. Immunol., vol. 14, pp. 315-328 (2014).
Ledford et al., "VP1 sequencing of all human rhinovirus serotypes: insights into genus phylogeny and susceptibility to antiviral capsid-binding compounds." J. Virol., vol. 78, pp. 3663-3764 (2004).
Lu et al., "Species comparison in P450 induction: effects of dexamethasone, omeprazole, and rifampin on P450 isoforms 1A and 3A in primary cultured hepatocytes from man, Sprague-Dawley rat, minipig, and beagle dog." Chem. Biol. Interact., vol. 134(3), pp. 271-281 (2001).
Ma et al., "Duration of pleconaril effect on cytochrome P450 3A activity in healthy adults using the oral biomarker midazolam." Drug Metabol. Dispo. vol. 34, pp. 783-785 (2006).
Ma et al., "The Effect of Oral Pleconaril on Hepatic Cytochrome P450 3A Activity in Healthy Adults Using Intravenous Midazolam as a Probe." J. Clin. Pharmacol., vol. 46, pp. 103-108 (2006).
Makarov et al., "Pyrazolopyrimidines: Potent Inhibitors Targeting the Capsid of Rhino- and Enteroviruses." ChemMedChem, vol. 20, pp. 1629-1634 (2015).
Makela et al., "Viruses and bacteria in the etiology of the common cold." J. Clin. Microbiol., vol. 36, pp. 539-542 (1998).
Malmstrom et al., "Human rhinovirus in bronchial epithelium of infants with recurrent respiratory symptoms." J. Allergy Clin. Immunol., vol. 118, pp. 591-596 (2006).
Matz, "Vapendavir significantly improves upper respiratory symptoms of naturally acquired rhinovirus infection asthmatic adults: Results of a phase 2 clinical trial." Eur. Respir. J., vol. 42, Publication No. 1493 (2013).
McKinlay et al., "Prevention of human poliovirus-induced paralysis and death in mice by the novel antiviral agent arildone." Antimicrob. Agents Chemother., vol. 22, pp. 1022-1025 (1982).
McSharry et al., "Inhibition of uncoating of poliovirus by arildone, a new antiviral drug." Virology, vol. 97, pp. 307-315 (1979).
Miller et al., "Rhinovirus-Associated Hospitalizations in Young Children." J. Infect. Dis., vol. 195, pp. 773-781 (2007).
Notice of Publication corresponding to European Patent Application No. 20867155.2 dated Jun. 15, 2022.
Palmenberg et al., "Classification and Evolution of Human Rhinoviruses." Meth. Mol. Biol., vol. 1221, pp. 1-10 (2015).
Pevear et al., "Activity of Pleconaril against Enteroviruses." Antimicrob. Agents Chemother., vol. 43, pp. 2109-2115 (1999).
PubChem CID 51323276, create date May 3, 2011.
Quillardet et al., "The SOS chromotest: a review." Mutation Res., vol. 297(3), pp. 235-279 (1993).
Quillardet et al., "SOS chromotest, a direct assay of induction of an SOS function in *Escherichia coli* K-12 to measure genotoxicity." Proc. Natl. Acad. Sci. USA, vol. 79, pp. 5971-5975 (1982).
Rossmann et al., "Picornavirus-receptor interactions." Trends Microbiol., vol. 10, pp. 324-331 (2002).
Rotbart et al., "Treatment of Potentially Life-Threatening Enterovirus Infections with Pleconaril." Clin. Infect. Dis., vol. 32, pp. 228-235 (2001).
Rotbart, "Antiviral Therapy for Enteroviruses and Rhinoviruses." Antivir. Agents Chemother., vol. 11, pp. 261-271 (2000).
Salorinne et al., "Polymorphic and solvate structures of ethyl ester and carboxylic acid derivatives of WIN 61893 analogue and their stability in solution." Cryst. Eng. Comm., vol. 16, pp. 9001-9009 (2014).
Schmidtke et al., "A rapid assay for evaluation of antiviral activity against coxsackie virus B3, influenza virus A, and herpes simplex virus type 1." J. Virol. Methods, vol. 95, pp. 133-143 (2001).
Senior, "FDA panel rejects common colds treatment." Lancet Infect. Dis., vol. 2, p. 264 (2002).
Steinke et al., "Immune Responses in Rhinovirus-Induced Asthma Exacerbations." Curr. Allergy Asthma Rep., vol. 16, Article No. 78 (8 pages) (2016).
Thurman et al., "Effects of Hormonal Contraception on Antiretroviral Drug Metabolism, Pharmacokinetics, and Pharmacodynamics." Am. J. Reprod. Immunol., vol. 71, pp. 523-530 (2014).
Whiting, "Animal Pharmacology of Nicardipine and Its Clinical Relevance." Am. J. Cardiol., vol. 59, pp. 3J-8J (1987).
Intention to Grant corresponding to European Patent Application No. 20867155.2 dated Nov. 18, 2024.
Egorova, A., et al., "Novel pleconaril derivatives: Influence of substituents in the isoxazole and phenyl rings on the antiviral activity against enteroviruses," European Journal of Medicinal Chemistry, vol. 188, pp. 1-16, 2020.

* cited by examiner

ISOXAZOLE-3-CARBOXAMIDE DERIVATIVES AND THEIR USE FOR TREATMENT OF DISEASES CAUSED BY VIRUS INFECTION

CROSS-REFERENCE TO RELATED APPLICATIONS

This application claims benefit of U.S. Provisional Patent Application Ser. No. 62/907,231, filed Sep. 27, 2019, and U.S. Provisional Patent Application Ser. No. 62/950,546, filed Dec. 19, 2019, each of which is herein incorporated by reference in its entirety.

TECHNICAL FIELD

The presently disclosed subject matter relates to 5-(3-{4-[5-(trifluoromethyl)-1,2,4-oxadiazol-3-yl]phenoxy}propyl) isoxazole-3-carboxamide derivatives and their use for the treatment of infections and diseases caused by viruses in mammals or other animals, especially diseases caused by entero- and rhinoviruses.

BACKGROUND

Multiple rhino-, coxsackie- and enteroviruses (RV, CV and EV, respectively) belong to the Enterovirus genus of the Picornaviridae family. They cause human viral diseases such as, but not limited to, the common cold, acute and chronic myocarditis, and paralytic poliomyelitis. To date, no vaccines (except for poliovirus) or drugs for the treatment or prevention of these viral infections have been approved.

Accordingly, there is an ongoing need for new compositions and methods of treating and/or preventing infections caused by viruses of the Enterovirus genus and/or the Picornaviridae family, such as rhinoviruses, coxsackieviruses, and enteroviruses.

SUMMARY

In some embodiments, the presently disclosed subject matter provides a compound of the formula (I):

(I)

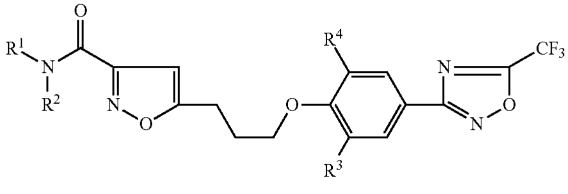

wherein: $R^1$ and $R^2$ are independently selected from H, a saturated or unsaturated, linear or branched $C_1$-$C_5$ alkyl, and benzyl, or wherein $R^1$ and $R^2$ together are $C_3$-$C_6$ alkylene; and $R^3$ and $R^4$ are independently selected from H, fluoro (F), chloro (Cl), methyl (Me), methoxy (OMe), trifluoromethyl ($CF_3$), and nitro ($NO_2$). In some embodiments, one or both of $R^3$ and $R^4$ are methyl. In some embodiments, one or both of $R^3$ and $R^4$ are fluoro.

In some embodiments, the compound of Formula (I) is selected from: N,N-dialkyl-5-(3-{2-methyl-4-[5-(trifluoromethyl)-1,2,4-oxadiazol-3-yl]phenoxy}-propyl)isoxazole-3-carboxamide, N,N-dialkyl-5-(3-{2-fluoro-4-[5-(trifluoro-methyl)-1,2,4-oxadiazol-3-yl]phenoxy}propyl) isoxazole-3-carbox-amide, and N,N-dialkyl-5-(3-{2-nitro-4-[5-(trifluoromethyl)-1,2,4-oxadiazol-3-yl]phenoxy}-propyl)isoxazole-3-carboxamide. In some embodiments, the compound is N,N-dimethyl-5-(3-{2-methyl-4-[5-(trifluoromethyl)-1,2,4-oxadiazol-3-yl]phen-oxy}propyl)isoxazole-3-carboxamide.

In some embodiments, the presently disclosed subject matter provides a pharmaceutical composition comprising a compound of Formula (I):

(I)

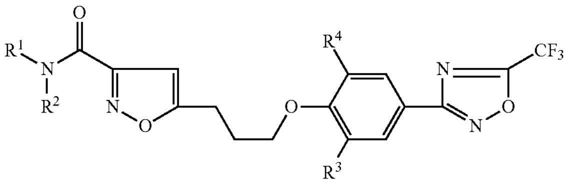

wherein: $R^1$ and $R^2$ are independently selected from H, a saturated or unsaturated, linear or branched $C_1$-$C_5$ alkyl, and benzyl, or wherein $R^1$ and $R^2$ together are $C_3$-$C_6$ alkylene; and $R^3$ and $R^4$ are independently selected from H, fluoro (F), chloro (Cl), methyl (Me), methoxy (OMe), trifluoromethyl ($CF_3$), and nitro ($NO_2$); and a pharmaceutically acceptable carrier.

In some embodiments, the presently disclosed subject matter provides the compound N,N-dimethyl-5-(3-{2-methyl-4-[5-(trifluoromethyl)-1,2,4-oxadiazol-3-yl]phenoxy}propyl)isoxazole-3-carboxamide for use in a therapeutic or prophylactic treatment of a disease caused by an enterovirus or rhinovirus infection, optionally in combination with one or more additional therapeutic agents.

In some embodiments, the presently disclosed subject matter provides a compound of Formula (I) for use in a therapeutic or prophylactic treatment of a disease caused by a picornavirus infection, optionally in combination with one or more additional therapeutic agents. In some embodiments, the picornavirus infection is a rhinovirus infection. In some embodiments, the picornavirus infection is an enterovirus infection. In some embodiments, the disease is acute flaccid myelitis or hand-foot-and-mouth disease.

In some embodiments, the presently disclosed subject matter provides a compound of Formula (I) for use in a therapeutic or prophylactic treatment of an influenza A viral infection, optionally wherein the influenza A viral infection is an infection of influenza A, subtype H1N1.

In some embodiments, the presently disclosed subject matter provides a method of treating or preventing a picornavirus infection in a subject in need thereof, the method comprising administering to the subject an effective amount of a compound of Formula (I). In some embodiments, the subject is an animal, optionally a human. In some embodiments, the picornavirus infection is a rhinovirus infection or an enterovirus infection. In some embodiments, the picornavirus infection is a pleconaril-resistant picornavirus infection. In some embodiments, the compound is N,N-dimethyl-5-(3-{2-methyl-4-[5-(trifluoromethyl)-1,2,4-oxadiazol-3-yl]phenoxy}-propyl)isoxazole-3-carboxamide. In some embodiments, the method further comprises administering one or more additional therapeutic agents to the subject, optionally wherein the one or more additional therapeutic agents comprise an antiviral agent.

In some embodiments, the presently disclosed subject matter provides a method of treating or preventing an influenza A virus infection, optionally an influenza A subtype H1N1 virus infection, in a subject in need thereof, wherein the method comprises administering to the subject a compound of Formula (I).

In some embodiments, the presently disclosed subject matter provides a method of treating or preventing a disease or condition caused by a viral infection, optionally a picornavirus infection or an influenza A viral infection, in a subject in need thereof, wherein the method comprises administering to the subject a compound of Formula (I). In some embodiments, the disease or condition caused by a viral infection is selected from the group comprising influenza, common cold, aseptic meningitis, encephalitis, hand-foot-and-mouth disease, paralytic poliomyelitis, conjunctivitis, diarrhea, herpetic angina, acute myocarditis, chronic myocarditis, sinusitis, otitis media, and acute flaccid myelitis. In some embodiments, the compound is N,N-dimethyl-5-(3-{2-methyl-4-[5-(trifluoromethyl)-1,2,4-oxadiazol-3-yl]phenoxy}propyl)isoxazole-3-carboxamide.

Accordingly, it is an object of the presently disclosed subject matter to provide isoxazole-3-carboxamide derivatives of Formula (I), pharmaceutical compositions thereof, and methods of using the derivatives to treat or prevent viral infections and the diseases or conditions caused by the viral infections.

An object of the presently disclosed subject matter having been stated hereinabove, and which is achieved in whole or in part by the presently disclosed subject matter, other objects will become evident as the description proceeds hereinbelow.

BRIEF DESCRIPTION OF THE DRAWINGS

FIG. 3A shows the blood virus (viremia) titers at day 1 post-infection. FIG. 3B shows the blood virus (viremia) titers at day 3 post infection. (****P<0.0001).

FIG. 4A shows lung virus titers on day 1 post infection. FIG. 4B shows lung virus titers on day 3 post-infection. FIG. 4C shows lung virus titers on day 5 post-infection. On days 1 and 3 post-infection only the guanidine-treated group showed a reduction in virus titers compared to placebo. However, on day 5 post-infection mice treated with the 30 mg dose of compound 8 also showed a reduction in virus titer. (*P<0.05, ***P<0.001).

(FIG. 6B). In addition, all doses of compound 8 decreased IL-5 on day 1 p.i. (FIG. 6B), but the 30 mg treatment increased IL-6 on day 3 p.i. (FIGS. 6B and 6C). In each of FIGS. 6A-6D, each set of six data bars is as follows, from left to right: placebo (filled bar), 100 mg/kg/d compound 8 (bar filled with offset rectangles), 30 mg/kg/d compound 8 (bar filled with checkerboard pattern), 10 mg (crosshatched bar), 100 mg/kg/d guanidine (bar filled with vertical lines), normal controls (bar filled with slanted lines). (*P<0.05).

(FIG. 7C) and the 10 mg dose decreased IFNγ on day 1 p.i. (FIG. 7D). Other changes included guanidine treatment increasing IL-12p70 on day 3 p.i. (FIG. 7A) and decreasing MCP-1 (FIG. 7C) on days 1 and 3 p.i. In each of FIGS. 7A-7D, each set of six data bars is as follows, from left to right: placebo (filled bar), 100 mg/kg/d compound 8 (bar filled with offset rectangles), 30 mg/kg/d compound 8 (bar filled with checkerboard pattern), 10 mg (crosshatched bar), 100 mg/kg/d guanidine (bar filled with vertical lines), normal controls (bar filled with slanted lines). (*$P<0.05$, $P<0.01$, *$P<0.001$).

(FIG. 8B) and all doses of compound 8 decreased GM-CSF and RANTES on day 1 p.i. (FIGS. 8C and 8D). Other observations included guanidine treatment increasing MIP-1a on day 5 p.i. (FIG. 8B) and decreasing GM-CSF and RANTES on day 1 p.i. (FIGS. 8C and 8D). In each of FIGS. 8A-8D, each set of six data bars is as follows, from left to right: placebo (filled bar), 100 mg/kg/d compound 8 (bar filled with offset rectangles), 30 mg/kg/d compound 8 (bar filled with checkerboard pattern), 10 mg (crosshatched bar), 100 mg/kg/d guanidine (bar filled with vertical lines), normal controls (bar filled with slanted lines). (*$P<0.05$, $P<0.01$, *$P<0.001$, ****$P<0.0001$).

DETAILED DESCRIPTION

Figure 1:
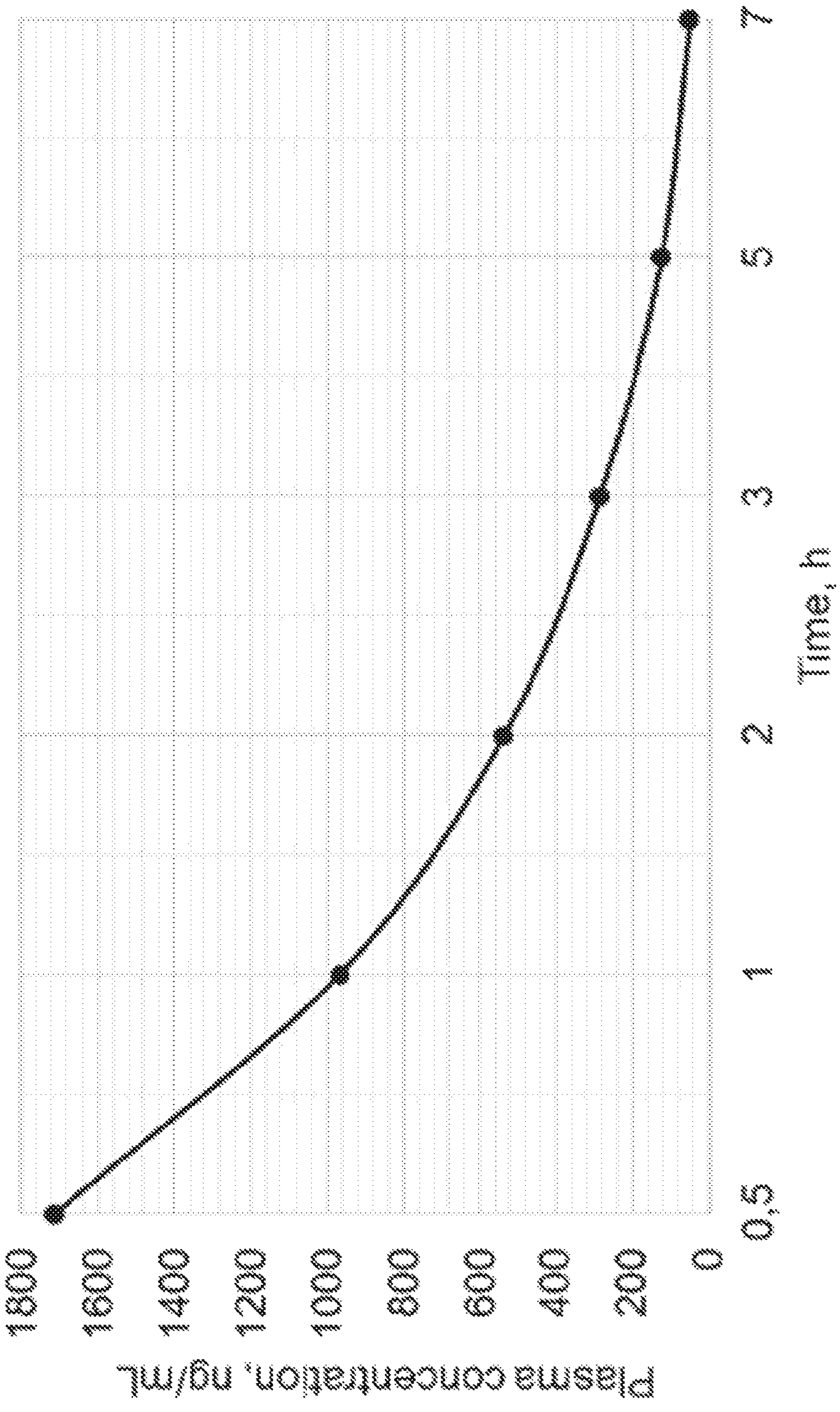
FIG. 1: Plasma concentration (measured in nanograms per milliliter (ng/ml) versus time (measured in hours) of N,N-dimethyl-5-(3-{2-methyl-4-[5-(trifluoromethyl)-1,2,4-oxadiazol-3-yl]phenoxy}propyl)isoxazole-3-carbox-amide, also referred to herein as Compound 8 or 11526092, an exemplary isoxazole-3-carboxamide of the presently disclosed subject matter, following oral administration of a 100 milligram per kilogram body weight dose FIG. 2: Percentage of initial body weight of mice infected with enterovirus D68 (EV D68) following treatment with Compound 8 (also referred to herein as 11526092) at a dose of 10 (unfilled squares), 30 (filled squares), or 100 (unfilled circles) milligrams per kilogram body weight per day (mg/kg/d). Percentage of initial body weight is provided for days 1-5 post-infection. For comparison, the percentage of initial body weight of infected mice treated with 100 mg/kg/d guanidine (filled triangles), a placebo (filled circles), and uninfected mice (Normal Controls, unfilled triangles) is also shown. Treatment with Compound 8 at 100 mg/kg/d protected mice from weight loss following infection. (***P<0.001).

The presently disclosed subject matter will now be described more fully. The presently disclosed subject matter can, however, be embodied in different forms and should not be construed as limited to the embodiments set forth herein below and in the accompanying Examples. Rather, these embodiments are provided so that this disclosure will be thorough and complete, and will fully convey the scope of the embodiments to those skilled in the art.

All references listed herein, including but not limited to all patents, patent applications and publications thereof, and scientific journal articles, are incorporated herein by reference in their entireties to the extent that they supplement, explain, provide a background for, or teach methodology, techniques, and/or compositions employed herein.

I. DEFINITIONS

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long-standing patent law convention, the terms "a", "an", and "the" refer to "one or more" when used in this application, including the claims.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" can mean at least a second or more.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

Unless otherwise indicated, all numbers expressing quantities of time, concentration, dosage and so forth used in the specification and claims are to be understood as being modified in all instances by the term "about".

Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value is meant to encompass variations of in one example ±20% or +10%, in another example ±5%, in another example ±1%, and in still another example ±0.1% from the specified amount, as such variations are appropriate to perform the disclosed methods.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "alkylene" refers to a bivalent alkyl group, where the bivalent alkyl group can be saturated or unsaturated and optionally substituted by one or more alkyl group substituents. In some embodiments, the alkylene group can include one or more oxygen atoms inserted in the carbon chain.

When the term "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

II. GENERAL CONSIDERATIONS

Lower respiratory tract infections (LRIs) represent the main cause of death in low income economies and the third largest cause of death worldwide (WHO. The top 10 causes of death 2018). In addition to influenza viruses, enteroviruses (EVs), coxsackieviruses (CVs) and rhinoviruses (RVs) of the Enterovirus genus of the Picornaviridae family frequently cause LRIs (Malmstrom K., Pitkaranta A., Carpen O., et al. J Allergy Clin Immunol. 2006, 118, 591; Miller E. K., Lu X., Erdman D. D., et al. The Journal of infectious diseases. 2007, 195, 773; Toivonen L., Schuez-Havupalo L., Karppinen S., et al. The Journal of infection. 2013, 66, 494). RVs are also the most commonly isolated viruses from patients with mild upper respiratory diseases (e.g., common cold) (Makela M. J., Puhakka T., Ruuskanen O., et al. Journal of clinical microbiology. 1998, 36, 539). RVs can also trigger sinusitis (DeMuri G. P., Gern J. E., Moyer S. C., et al. J Pediatr. 2016, 171, 133-9 el.) and otitis media (Toivonen L, Schuez-Havupalo L, Karppinen S, et al. Pediatrics. 2016; 138(3).). In addition, RV infections can exacerbate asthma (Corne J M, Marshall C, Smith S, et al. Lancet. 2002, 359, 831; Steinke J. W., Borish L. Curr Allergy Asthma Rep. 2016, 16, 78). EVs and CVs cause a wide range of acute and chronic diseases, such as, but not limited to, aseptic meningitis, encephalitis, hand-foot-and-mouth disease, conjunctivitis, diarrhea, herpetic angina, acute and chronic myocarditis, and respiratory diseases (Melnick J. L. Poliovirus and other enteroviruses. In: Evans A S, Kaslow R A, editors. Viral infections of humans: epidemiology and control. New York: Plenum Publishing; 1997. p. 583-663). It has also been suggested that acute flaccid myelitis, which leads to loss of limb control in young children, can be due to EV-68.

Current treatment of EV, CV and RV infections aims to reduce and shorten symptoms (e.g. fever and pain, fatigue, and nasal blockage in the case of common cold). There is no effective antiviral treatment, and with the exception of poliovirus, no prophylaxis, to prevent the millions of lost school and working days caused by EVs, CVs and RVs (Rotbart H. A. Antivir. Agents Chemother. 2000, 11, 261). Vaccine development is complicated by the multiplicity of serotypes. About 100 human EV serotypes and more than 160 RV serotypes (Palmenberg A. C., Gern J. E. Methods in molecular biology. 2015, 1221, 1) exist with most having epidemiological significance (The Picornaviridae. Enterovirus. 2018).

Because of the issues with vaccine generation, the development of effective antivirals can be an attractive alternative. Considering the number of serotypes, effort has focused on the discovery of drugs with broad spectrum activity. Cellular proteins (e.g. cellular receptors such as inter-cellular adhesion molecule 1 (ICAM-1) for human rhinoviruses) and viral proteins that are highly conserved among serotypes (e.g. protease, polymerase, hydrophobic pocket in VP1) represent potential targets for inhibitors acting against multiple serotypes and thus have broad-spectrum activity. For example, compounds binding to the viral protease, polymerase or into a small hydrophobic pocket in capsid protein 1 (VP1) have been developed that inhibit multiple serotypes in vitro (De Palma A. M., Vliegen I., De Clercq E., Neyts J. Med. Res. Rew. 2008, 28, 823). The promising results have been obtained with the capsid-binding inhibitors pleconaril and vapendavir (Pevear D. C., Tull T. M., Seipel M. E., Groarke J. M. Antimicrob. Agents Chemother. 1999, 43, 2109; Matz J. The European respiratory journal, 2013, 42, 1493). However, due to insufficient effectiveness and/or side effects in the clinic, neither of these inhibitors has been approved by the FDA to date (Senior K. The Lancet Infectious diseases. 2002, 2, 264).

More particularly, VP1 is one of the four viral capsid proteins (i.e., VP1-4; each having 60 copies) composing the icosahedral capsid of picornaviruses (about 30 nm in diameter), which are cleaved from the precursor protein P1. Together with VP2 and VP3, VP1 is found on the external surface of the capsid, while VP4 is located inside the capsid. The capsid proteins pack the viral genome, a single-stranded RNA of positive polarity (mRNA-like structure), via interactions with VP4. The three surface proteins VP1-3 do not have appreciable amino acid sequence homology. However, all three form an eight-stranded anti-parallel ß-barrel. Its wedged shape facilitates VP1, 2, and 3 assembly into an icosahedral viral capsid. The amino acid loops between the ß-strands and the N- and C-terminal sequences are structurally different and determine the morphology and antigenicity of distinct EV and RV (Racaniello V R. Picornaviridae: the viruses and their replication. In: Knipe D M, Howley P M, Griffin D E, editors. Fields Virology. Philadelphia: Lippincott Williams & Wilkins; 2006. p. pp. 795-838).

Generally, capsid morphology is characterized by a star-shaped plateau at the 5-fold axis of capsid symmetry. It is surrounded by a deep depression (called a canyon) in most EV and RV. Just beneath the canyon floor is a hydrophobic pocket that can be empty (e.g. in RV-B14) or is filled with a lipped, sphingosine or fatty acid (called a pocket factor) in the majority of EV and RV. The amino acids of the hydrophobic pocket are highly conserved across EV and also RV, whereas at distinct amino acid positions a polymorphism can exist (Ledford R M, Patel N R, Demenczuk T M, et al. Journal of virology. 2004, 78, 3663). Another protrusion has been detected at the 3-fold axis of symmetry. The external localization of VP1-3 predisposes their interaction with surface molecules of immune and host cells (VP1-3). Their loops act as antigenic sites. The canyon enables binding of cell surface molecules (e.g. ICAM, LDL, DAF, or CAR) for viral attachment to susceptible host cells (Rossmann M. G., He Y., Kuhn R. Trends in microbiology. 2002, 10, 324-31).

Receptor binding induces structural changes in the viral capsid triggering the release of the pocket factor and subsequently capsid destabilization. The viruses penetrate into the host cell and release their genomic RNA into the cytoplasm (uncoating) where replication of picornaviruses takes place. After interaction of the positive-stranded viral RNA with host cell ribosomes, a polyprotein is translated and then cleaved into individual viral proteins (capsid proteins and non-structural proteins) by viral proteases 2A and 3C/3CD. The RNA-dependent polymerase synthesizes the minus strand matrix from the surface of the plus strand and uses it to replicate the genome. Viral protein synthesis and RNA replication run in parallel to produce a huge number of virus protein and RNA genome copies. Once a critical amount of viral structural proteins is reached, they begin to assemble and form protomers which further assemble into pentamers to form the capsid. After interaction of the capsid proteins with the genome, progeny virion are produced. They are released from the host cell by means of lysis (Racaniello V R. Picornaviridae: the viruses and their replication. In: Knipe D M, Howley P M, Griffin D E, editors. Fields Virology. Philadelphia: Lippincott Williams & Wilkins; 2006. p. pp. 795-838).

The development of anti-picornaviral compounds with the capsid-binding mechanism of action began with synthesis of compounds by Sterling-Winthrop Company, widely known as WIN-compounds (reviewed in Egorova A. Eur J Med Chem. 2019, 178, 606-622). It was discovered that some #-diketones from a synthetic library were active against equine rhinovirus during the course of screening for new antivirals (Diana G. D., Salvador U. J., Zalay E. S., et al. J. Med. Chem. 1977, 20, 757; Diana G. D., Salvador U. J., Zalay E. S., J. Med. Chem. 1977, 20, 750-6; Diana G. D., Carabateas P. M., Johnson R. E., et al, J. Med. Chem. 1978, 21, 889; Diana G. D., Carabateas P. M., Salvador U. J., et al. J. Med. Chem. 1978, 21, 689). Several modifications of the structure were performed with a view to improving antiviral activity and resulted in the formation of arildone (also known as WIN 38020). Arildone specifically inhibits replication of poliomyelitis virus in vitro through prevention of virion uncoating, while in vivo it prevents poliovirus-induced paralysis and death in mice (McSharry J. J., Caliguiri L. A., Eggers H. J. Virology. 1979, 97, 307; Caliguiri L. A., McSharry J. J., Lawrence G. W. et al. Virology. 1980, 105(1):86-93; McKinlay M. A., Miralles J. V., Brisson C. J., Pancic F. Antimicrob. Agents Chemother. 1982, 22, 1022). Ultimately, after many years of research in the field, the most advanced compound, pleconaril, was tested on 215 clinical isolates of enterovirus serotypes and demonstrated activity ($IC_{50} \leq 0.03$ μM and $CC_{90}$ inhibition ≤0.18 μM) with most of them (Pevear D. C., Tull T. M., Seipel M. E., Groarke J. M. Antimicrobial agents and chemotherapy. 1999, 43, 2109).

The development of pleconaril resulted from several modifications of the oxadiazole ring of an earlier analog called disoxaril. Pleconaril contains a trifluoromethyl oxadiazole that does not experience hydroxylation of the methyl group on the oxadiazole ring. Pleconaril is therefore protected from metabolism. Interestingly, this orally bioavailable and systemic-acting small molecule inhibitor possesses a broad-spectrum activity against enteroviruses as well as rhinoviruses. Pleconaril inhibited over 100 tested RV serotypes and 95% of non-polio enteroviruses at a compound concentration of 100 ng/mL or less (Pevear D. C., Tull T. M., Seipel M. E., Groarke J. M. Antimicrob. Agents Chemother. 1999, 43, 2109). However, due to the existence of pleconaril-resistant enteroviruses, for instance coxsackievirus B3 variants, there is a need for optimization of the compound structure. In 2002 pleconaril (Picovir) failed to win FDA approval for the treatment of the common cold due to a large number of pleconaril-resistant viruses (Heinz B. A., Rueckert R. R., Shepard D. A. Journal of Virology. 1989, 63, 2476) and the presence of adverse effects, including an association with menstrual irregularities in women taking oral contraceptives (Hayden F. G., Herrington D. T., Coats T. L. Clinical infectious diseases: an official publication of the Infectious Diseases Society of America. 2003, 36, 1523). Studies have also demonstrated that this compound results in induction of cytochrome P450 3A4 (CYP3A4) (Ma J. D., Nafziger A. N., Rhodes G., Journal of clinical pharmacology. 2006, 46, 103; Ma J. D., Nafziger A. N., Rhodes G. Drug metabolism and disposition: the biological fate of chemicals. 2006, 34, 783), providing a likely explanation for the impact on oral contraceptive function. There has been limited efforts to follow up on this observation.

Pleconaril was the closest an antiviral drug has come as a potential treatment for the treatment of the common cold. The most recent clinical failure of note is another potential anti-picornaviral drug, Vapendavir, which failed in Phase IIb for treatment of rhinoviral infections in patients with asthma in February 2017 (likely due to better-than-expected improvements in control groups (Anon. Aviragen Therapeutics Announces Top-Line Results from Phase 2b SPIRITUS Trial of Vapendavir 2017). Thus, the development of effective capsid-binding inhibitors with broad-spectrum activity is a problem that has yet to be solved.

The hydrophobic pocket within viral capsid protein 1 is a promising target to combat picornaviruses using small molecules. Except coxsackievirus B3, all known enterovirus variants with full resistance toward capsid-binding inhibitors have mutations of residues directly involved in the formation of the hydrophobic binding pocket. In case of coxsackievirus B3, substitutions have been also reported outside the binding pocket causing this type of capsid-binding inhibitor resistance: I1207K and I1207R of the viral capsid protein 1. Both substitutions completely abolish the antiviral activity of pleconaril but do not affect coxsackievirus B3 replication rates in vitro.

The presently disclosed subject matter relates to a new generation of derivatives of the capsid-binding inhibitor pleconaril with promising broad-spectrum activities against viruses (e.g., RVs and CVs) and good safety and pharmacokinetic profile. As described further in the examples below, an exemplary pleconaril derivative of the presently disclosed subject matter, i.e., N,N-dimethyl-5-(3-{2-methyl- 4-[5-(trifluoromethyl)-1,2,4-oxadiazol-3-yl]phen-oxy}-propyl)isoxazole-3-carbox-amide, inhibited the replication of a broad spectrum of EV in vitro with $IC_{50}$ values between 0.04 and 0.64 μM for viruses resistant to pleconaril, without affecting cytochrome P450 enzyme activity.

III. COMPOUNDS OF FORMULA (I)

In some embodiments, the presently disclosed subject matter provides isoxazole derivatives (i.e., isoxazole 3-carboxamide derivatives) with broad spectrum antiviral activity (including activity against pleconaril resistant strains) and low CYP3A4 induction.

In some embodiments, the presently disclosed subject matter provides a compound of the Formula (I):

(I)

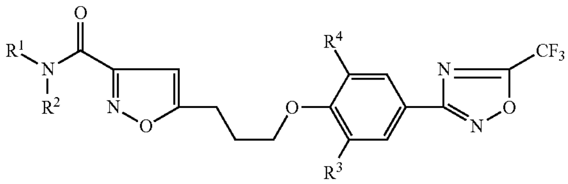

wherein $R^1$ and $R^2$ are independently selected from H, $C_1$-$C_5$ alkyl (i.e., a saturated or unsaturated, linear or branched aliphatic radical having 1-5 chain members), and benzyl, or wherein $R^1$ and $R^2$ together are $C_3$-$C_6$ alkylene (i.e., a aliphatic chain comprising three to six carbon atoms); and $R^3$ and $R^4$ are independently selected from H, fluoro (F), chloro (Cl), methyl (Me), methoxy (OMe), trifluoromethyl ($CF_3$), and nitro ($NO_2$). In some embodiments, one or both of $R^3$ and $R^4$ are methyl. In some embodiments, one or both of $R^3$ and $R_4$ are F. In some embodiments, the compound of Formula (I) is selected from the group comprising compounds 1-13 described in the Examples below.

In some embodiments, the presently disclosed subject matter provides compounds of Formula (I) selected from the group comprising:

N,N-dialkyl-5-(3-{2-methyl-4-[5-(trifluoromethyl)-1,2,4-oxadiazol-3-yl]-phenoxy}propyl)isoxazole-3-carboxamide, N,N-dialkyl-5-(3-{2-fluoro-4-[5-(trifluoromethyl)-1,2,4-oxadiazol-3-yl]-phenoxy}propyl)isoxazole-3-carboxamide, and N,N-dialkyl-5-(3-{2-nitro-4-[5-(trifluoromethyl)-1,2,4-oxadiazol-3-yl]-phenoxy}propyl)isoxazole-3-carboxamide.

In some embodiments, the presently disclosed subject matter provides at least one compound selected from the group comprising:

N,N-dimethyl-5-(3-{2-methyl-4-[5-(trifluoromethyl)-1,2,4-oxadiazol-3-yl]-phenoxy}propyl)isoxazole-3-carboxamide, and N,N-dimethyl-5-(3-{2-nitro-4-[5-(trifluoromethyl)-1,2,4-oxadiazol-3-yl]-phenoxy}propyl)isoxazole-3-carboxamide.

In some embodiments, the compound of Formula (I) is N,N-dialkyl-5-(3-{2-methyl-4-[5-(trifluoromethyl)-1,2,4-oxadiazol-3-yl]phenoxy}propyl)isoxazole-3-carboxamide.

In some embodiments, the presently disclosed the presently disclosed subject matter provides a pharmaceutically acceptable salt of a compound of Formula (I) (such as a hydrochloride, sulphate, acetate, trifluoroacetate, maleate, fumarate salt or another salt as described hereinbelow) and/or a solvate thereof.

The compounds of the Formula (I) exhibit strong antiviral activity, especially against picornaviruses with $IC_{50}$ in the range of ~0.008-15 μM, as determined by the method described by Schmidtke M., Hammerschmidt E., Schuler S., et al. J Antimicrob. Chemother. 2005, 56, 648. Typical results are given in Example 15, below. The compounds of the presently disclosed subject matter demonstrate a high level of selectivity for virus and are not active on bacteria or human cells, which should reduce the potential for adverse side effects.

Selected compounds of the Formula (I) of the presently disclosed subject matter were tested for potential mutagenicity using the SOS-chromotest (Quillardet P., Huisman O., D'Ari R., Hofnung M., Proc. Natl. Acad. Sci. USA, 1982, 79, 5971-5) and found to be non-mutagenic at 25-50 pg per spot.

The compounds of Formula (I) can be synthesized by routes using chemical group transformations well known in the field of organic chemistry.

In some embodiments, the compounds can be synthesized by the route described in Scheme 1, below.

Scheme 1. Exemplary Synthetic Route of Compounds of Formula (I).

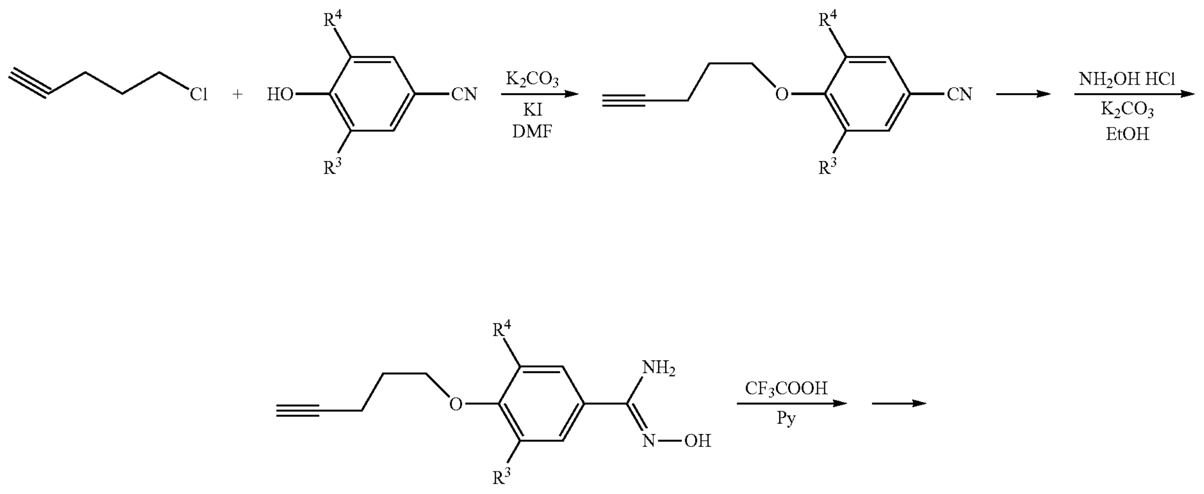

-continued

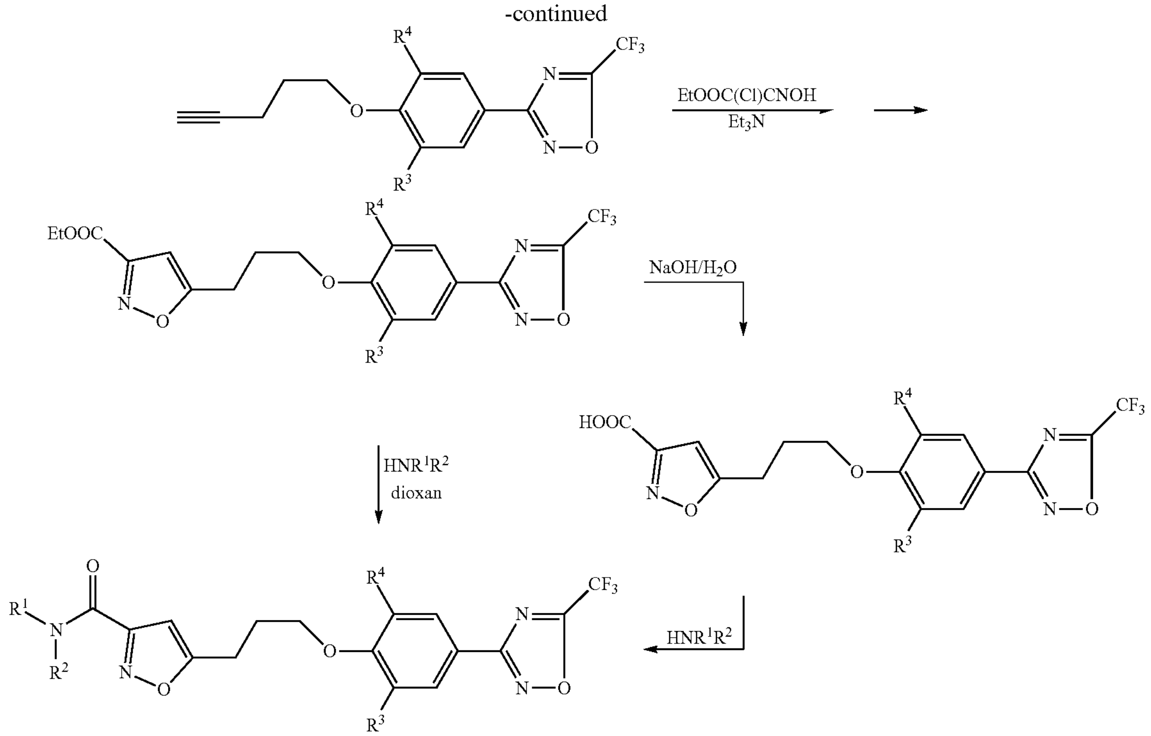

For instance, as shown in Scheme 1, a halo-substituted alkyne (e.g., 1-chloropent-4-yne) can be reacted with a para-cyano-substituted phenol compound, which can be optionally further substituted, e.g., on the carbon atoms adjacent to the phenol carbon, in the presence of a base (e.g., potassium carbonate) to form an ether. The cyano group can be transformed by reacting the ether compound with hydroxylamine hydrochloride in the presence of a base (e.g., potassium carbonate), thereby forming an N-hydroxy amidine, which is then reacted with trifluoroacetic acid to form a trifluoromethyl-substituted 1,2,4-oxadiazole group. Elaboration of the alkyne group by reacting the alkyne-containing intermediate with ethyl chloro(hydroxyamino)acetate results in the formation of an ester-substituted isoxazole ring. The ester-substituent on the isoxazole can undergo base-catalyzed hydrolysis to form a carboxylic acid and then contacted with an amine (e.g., a dialkylamine) to form the final carboxamide. Alternatively, the ester-substituted intermediate can be transformed directly into the final carboxamide by reaction with the amine.

In some embodiments, the presently disclosed subject matter provides a pharmaceutical composition comprising a compound of the Formula (I). For example, the pharmaceutical composition can include one or more compounds of Formula (I) and a pharmaceutically acceptable carrier. In some embodiments, the compounds of the presently disclosed subject matter are formulated for use by preparing a dilute solution or suspension in a pharmaceutically acceptable aqueous, organic, or aqueous-organic medium. In some embodiments, the compounds are formulated for topical or parenteral administration by intravenous, subcutaneous or intramuscular injection, or for intranasal application; or are prepared in tablet, capsule or aqueous suspension form with conventional excipients for oral administration or as a suppository.

Thus, in some embodiments, the compounds of the presently disclosed subject matter are provided for use in the treatment or prevention of picornavirus infections, such as for use in the treatment of entero- or rhinovirus infections, in humans and in animals. In some embodiments, the compounds of the presently disclosed subject matter are provided for use in the treatment or prevention of a disease or condition caused by (or triggered by) a picornavirus infection, such as for use in the treatment or prevention of a disease or condition caused by an entero- or rhinovirus infection, in humans and in animals.

In some embodiments, the presently disclosed subject matter relates the use of a compound of the Formula (I) in a method for the treatment or prophylaxis of viral infections in animals (e.g., humans or other mammals) or for the treatment or prophylaxis of a disease or condition caused or triggered by a viral infection. In some embodiments, the viral infection is a picornavirus infection. In some embodiments, the picornavirus infection is an enterovirus infection. In some embodiments, the disease caused by the enterovirus infection is acute flaccid myelitis or hand-foot-and-mouth disease. Thus, in some embodiments, the presently disclosed compounds are provided for use in treating or preventing acute flaccid myelitis or hand-foot-and-mouth disease. In some embodiments, the picornavirus infection is a rhinovirus infection. In some embodiments, the picornavirus infection is a coxsackievirus infection. In some embodiments, the picornavirus infection relates to the infection of a pleconaril-resistant strain of a picornavirus. In some embodiments, the viral infection is an influenza virus infection. In some embodiments, the influenza virus is an influenza A virus. In some embodiments, the influenza A virus is an influenza A virus subtype H1N1.

In some embodiments, the compounds of Formula (I) can be used in dosages from 0.001-1000 mg/kg body weight. In some embodiments, the compound of Formula (I) is used in combination with one or more additional therapeutic agents, e.g., one or more additional anti-viral therapeutic agents (i.e., an additional anti-viral therapeutic agent that is not a compound of Formula (I)) and/or one or more additional therapeutic agents used to treat a symptom of a viral infection or a disease caused or triggered by a viral infection or to enhance the immune response of a subject.

In some embodiments, the presently disclosed subject matter provides a method of treating or preventing a picornavirus infection in a subject in need thereof. In some embodiments, the method comprising administering to the subject an effective amount of a compound of Formula (I):

(I)

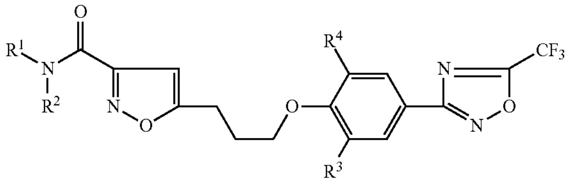

wherein $R^1$ and $R^2$ are independently selected from H, $C_1$-$C_5$ alkyl (i.e., a saturated or unsaturated, linear or branched aliphatic radical having 1-5 chain members), and benzyl, or wherein $R^1$ and $R^2$ together are $C_3$-$C_6$ alkylene (i.e., a aliphatic chain comprising three to six carbon atoms); and $R^3$ and $R^4$ are independently selected from H, F, Cl, Me, OMe, $CF_3$, and $NO_2$. In some embodiments, one or both of $R^3$ and $R^4$ are methyl. In some embodiments, one or both of $R^3$ and $R^4$ are F. In some embodiments, the compound of Formula (I) is selected from the group comprising compounds 1-13 described in the Examples below. In some embodiments, the compound of Formula (I) selected from the group comprising: N,N-dialkyl-5-(3-{2-methyl-4-[5-(trifluoromethyl)-1,2,4-oxadiazol-3-yl]phenoxy}propyl) isoxazole-3-carbox-amide, N,N-dialkyl-5-(3-{2-fluoro-4-[5-(trifluoromethyl)-1,2,4-oxadiazol-3-yl]phenoxy}propyl) isoxazole-3-carbox-amide, and N,N-dialkyl-5-(3-{2-nitro-4-[5-(trifluoromethyl)-1,2,4-oxadiazol-3-yl]phenoxy} propyl)isoxazole-3-carbox-amide. In some embodiments, the compound of Formula (I) is selected from N,N-dimethyl-5-(3-{2-methyl-4-[5-(trifluoromethyl)-1,2,4-oxadiazol-3-yl]phen-oxy}propyl)isoxazole-3-carbox-amide, and N,N-dimethyl-5-(3-{2-nitro-4-[5-(trifluoromethyl)-1,2,4-oxadiazol-3-yl]phenoxy}propyl)isoxazole-3-carbox-amide. In some embodiments, the compound of Formula (I) is N,N-dialkyl-5-(3-{2-methyl-4-[5-(trifluoromethyl)-1,2,4-oxadiazol-3-yl]phenoxy}propyl)isoxazole-3-carboxamide.

In some embodiments, the subject is a subject who has been diagnosed with a picornavirus infection. In some embodiments, the subject is a subject at higher risk for infection, e.g., due to being exposed to one or more subjects having a diagnosed infection or due to having a compromised immune system. Typically, the subject of the presently disclosed subject matter is an animal, e.g. a mammal. In some embodiments, the subject is a human. In some embodiments, the subject is a non-human mammal.

In some embodiments, the picornavirus infection is a rhinovirus infection or an enterovirus infection. In some embodiments, the picornavirus infection is a pleconaril-resistant picornavirus infection. In some embodiments, the administration of the compound of Formula (I) results in a lower level of CYP3A4 induction in hepatocytes (e.g., in the subject to whom the compound of Formula (I) is administered) than pleconaril (e.g., at the same dosage). In some embodiments, the compound of Formula (I) exhibits no appreciable binding to pregnane X receptor (PXR).

In some embodiments, the method further comprises administering to the subject one or more additional therapeutic agents, such as one or more additional antiviral agents and/or one or more agents used to treat a symptom or symptoms of a picornavirus infection or infection-related disease. Such additional therapeutic agents include, but are not limited to, analgesics, decongestants, anti-histamines, anti-inflammatory agents, and the like.

In some embodiments, the presently disclosed subject matter provides a method of treating or preventing a viral infection related to an influenza virus, in a subject in need thereof, wherein the method comprises administering to the subject a compound of Formula (I) as described hereinabove. In some embodiments, the subject is a human. In some embodiments, the subject is a non-human animal, e.g., a mammal. In some embodiments, the influenza virus is an influenza A virus. In some embodiments, the influenza virus is an influenza A subtype H1N1 virus. In some embodiments, the compound of Formula (I) is N,N-dimethyl-5-(3-{2-methyl-4-[5-(trifluoromethyl)-1,2,4-oxadiazol-3-yl] phen-oxy}-propyl)isoxazole-3-carboxamide.

In some embodiments, the presently disclosed subject matter provides a method of treating or preventing a disease or condition caused by a viral infection, optionally a picornavirus infection or an influenza A viral infection, in a subject in need thereof, wherein the method comprises administering to the subject a compound of Formula (I) as described hereinabove. In some embodiments, the subject is a human. In some embodiments, the subject is a non-human animal, e.g., a mammal. Diseases or conditions caused by viral infections include, but are not limited to, influenza, common cold, aseptic meningitis, encephalitis, hand-foot-and-mouth disease, paralytic poliomyelitis, conjunctivitis, diarrhea, herpetic angina, acute myocarditis, chronic myocarditis, sinusitis, otitis media, and acute flaccid myelitis. In some embodiments, the compound of Formula (I) is N,N-dimethyl-5-(3-{2-methyl-4-[5-(trifluoromethyl)-1,2,4-oxadiazol-3-yl]phenoxy}-propyl)isoxazole-3-carbox-amide. In some embodiments, the method can further comprise administering one or more additional therapeutic agents, such as an antiviral compound that is not of Formula (I) or a compound to treat or mitigate one or more symptom of the disease or condition (e.g., a therapeutic agent to treat cough or nasal congestion).

IV. PHARMACEUTICALLY ACCEPTABLE SALTS AND COMPOSITIONS

As noted above, in some embodiments, the compound of Formula (I) can be provided as a pharmaceutically acceptable salt. Such salts include, but are not limited to, pharmaceutically acceptable acid addition salts, pharmaceutically acceptable base addition salts, pharmaceutically acceptable metal salts, ammonium and alkylated ammonium salts, and combinations thereof.

Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like.

Base addition salts include but are not limited to, ethylenediamine, N-methyl-glucamine, lysine, arginine, ornithine, choline, N, N'-dibenzylethylenediamine, chloroprocaine, diethanolamine, procaine, N-benzylphenethylamine, diethylamine, piperazine, tris (hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like.

Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

In some embodiments, the presently disclosed compounds can further be provided as a solvate.

The compound of Formula (I) can be used on a sample either in vitro (for example, on isolated cells or tissues) or in vivo in a subject (i.e. living organism, such as a patient). In some embodiments, the subject or patient is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided are methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the treatment of livestock including, but not limited to domesticated swine (pigs and hogs), ruminants, horses, poultry, and the like.

In some embodiments, the compound of Formula (I) can include more than one of the compounds described herein. In some embodiments, the compound can be administered along with one or more additional therapeutic agents known in the art for treating a disease or disorder associated with a viral infection. For example, the compounds can be co-administered with an antiviral compound that is not a compound of Formula (I) or a therapeutic agent useful in treating a symptom of a viral infection (e.g., pain, fever, stuffy/runny nose, cough, inflammation, etc.). The compound of Formula (I) and the one or more other therapeutic agents can be provided in a single formulation or co-administered in separate formulations at about the same time or at different times (e.g., different times within the same day, week, or month).

In some embodiments, the compound of Formula (I) (which can also be referred to as the "active ingredient") can be administered in a pharmaceutically acceptable composition where the compound can be admixed with one or more pharmaceutically acceptable carriers. The term "pharmaceutically acceptable carrier" means a non-toxic material that does not interfere with the effectiveness of the biological activity of the active ingredients. In some embodiments, the pharmaceutically acceptable composition can also contain salts, buffering agents, preservatives, compatible carriers, and optionally other therapeutic agents.

Suitable methods for administration of a compound of Formula (I) or pharmaceutically acceptable composition thereof to a subject include, but are not limited to intravenous injection, oral administration, buccal, topical, subcutaneous administration, intraperitoneal injection, pulmonary, intanasal, intracranial injection, and rectal administration. The particular mode of administering a composition matter depends on various factors, including the distribution and abundance of cells to be treated and mechanisms for metabolism or removal of the composition from its site of administration.

An effective dose of a composition of the presently disclosed subject matter is administered to a subject. An "effective amount" is an amount of the composition sufficient to produce detectable treatment. Actual dosage levels of constituents of the compositions of the presently disclosed subject matter can be varied so as to administer an amount of the composition that is effective to achieve the desired effect for a particular subject and/or target. The selected dosage level can depend upon the activity of the composition and the route of administration. In some embodiments, the compounds of Formula (I) can be used in dosages from 0.001-1000 mg/kg body weight.

After review of the disclosure herein of the presently disclosed subject matter, one of ordinary skill in the art can tailor the dosages to an individual subject, taking into account the particular formulation, method of administration to be used with the composition, and nature of the target to be treated. Such adjustments or variations, as well as evaluation of when and how to make such adjustments or variations, are well known to those of ordinary skill in the art.

The therapeutically effective amount can be determined by testing the compounds in an in vitro or in vivo model and then extrapolating therefrom for dosages in subjects of interest, e.g., humans. The therapeutically effective amount should be enough to exert a therapeutically useful effect in the absence of undesirable side effects in the subject to be treated with the composition.

Pharmaceutically acceptable carriers are well known to those skilled in the art and include, but are not limited to, from about 0.01 to about 0.1M and preferably 0.05M phosphate buffer or 0.8% saline. Such pharmaceutically acceptable carriers can be aqueous or non-aqueous solutions, suspensions and emulsions. Examples of non-aqueous solvents suitable for use in the presently disclosed subject matter include, but are not limited to, propylene glycol, polyethylene glycol, vegetable oils such as olive oil, and injectable organic esters such as ethyl oleate. Aqueous carriers suitable for use in the presently disclosed subject matter include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the presently disclosed subject matter can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the presently disclosed subject matter include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellent.

Solid carriers suitable for use in the presently disclosed subject matter include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Parenteral carriers suitable for use in the presently disclosed subject matter include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the presently disclosed subject matter can be mixed as needed with disintegrants, diluents, granulating agents, lubricants, binders and the like using conventional techniques known in the art. The carriers can also be sterilized using methods that do not deleteriously react with the compounds, as is generally known in the art. The compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in *Remington: The Science and Practice of Pharmacy*, A. Gennaro, ed., 20th edition, Lippincott, Williams & Wilkins, Philadelphia, Pa.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Further, formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compounds can further be formulated for topical administration. Suitable topical formulations include one or more compounds in the form of a liquid, lotion, cream or gel. Topical administration can be accomplished by application directly on the treatment area. For example, such application can be accomplished by rubbing the formulation (such as a lotion or gel) onto the skin of the treatment area, or by spray application of a liquid formulation onto the treatment area.

In some formulations, bioimplant materials can be coated with the compounds so as to improve interaction between cells and the implant.

Formulations of the compounds can contain minor amounts of wetting or emulsifying agents, or pH buffering agents. The formulations comprising the compound can be a liquid solution, suspension, emulsion, tablet, pill, capsule, sustained release formulation, or powder. The compounds can be formulated as a suppository, with traditional binders and carriers such as triglycerides.

Oral formulations can include standard carriers such as pharmaceutical grades of mannitol, lactose, starch, magnesium stearate, polyvinyl pyrollidone, sodium saccharine, cellulose, magnesium carbonate, etc.

In some embodiments, the pharmaceutical composition comprising the compound of Formula (I) of the presently disclosed subject matter can include an agent which controls release of the compound, thereby providing a timed or sustained release compound.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

General Methods and Materials

Chemicals and solvents were purchased from Alfa Aesar (Haverhill, Mass., United States of America) or from Sigma-Aldrich (Sigma-Aldrich Company, St. Louis, Mo., United States of America). They were used without additional purification.

Melting points were determined according to the BP procedure and are uncorrected (Electrothermal 9001, Cole-Parmer, Stone, United Kingdom).

NMR spectra were determined with a Varian Unity Plus 300 (Varian Associates, Palo Alto, Calif., United States of America). Shifts for $^1H$ NMR are reported in parts-per-million (ppm) downfield from TMS.

Mass spectra were obtained using a Finnigan SSQ-700 instrument (Thermo Fisher Scientific, Waltham, Mass., United States of America) with direct injection.

Reactions and purity of compounds were controlled by thin-layer chromatography (TLC) using Silicagel 60 F254 aluminium sheets (Merck & Co., Inc., Kenilworth, N.J., United States of America).

General Procedure for the Synthesis of 5-(3-{4-[5-(trifluoromethyl)-1,2,4-oxadiazol-3-yl]phenoxy}propyl)isoxazole-3-carboxamide Derivatives The synthesis of key scaffold ethyl 5-(3-{2,6-$R^3R^4$-4-[5-(trifluoromethyl)-1,2,4-oxadiazol-3-yl]phenoxy}propyl)isoxazole-3-carboxylates were performed according a previous procedure (Salorinne K., Lahtinen T., Marjomskib V., Hskkinen H. CrystEngComm, 2014, 16, 9001).

A solution of 5.0 mmol of ethyl 5-(3-{2,6-$R^3R^4$-4-[5-(trifluoromethyl)-1,2,4-oxadiazol-3-yl]phenoxy}propyl)isoxazole-3-carboxylate in ethanol in heavy glass flask was treated by 15.0 ml of corresponding amine in the form of water solution or itself. The flask was close and heated at 50-70° C. for 0.5-2 hours. The solution was evaporated and residue treated by water. Solid was filtered off and crystallized from small volume of alcohol.

Example 1

N-benzyl-5-(3-{2,6-dimethyl-4-[5-(trifluoromethyl)-1,2,4-oxadiazol-3-yl]phenoxy}propyl)isoxazole-3-carboxamide (Compound 1)

Yield 52%. Mp. 102-4° C. Mass (EI), m/z ($I_{relat.}$(%)) 500.4699 $[M]^+$ (42). $C_{25}H_{23}F_3N_4O_4$.

$^1H$ NMR (300 MHz, DMSO-$d_6$): δ 2.13 (2H, dt, J=6.5, 7.7, $CH_2\underline{CH_2}CH_2$), 2.30 (6H, s, $ArCH_3$), 3.14 (2H, t, J=7.7, $CH_2Ar$), 3.92 (2H, t, J=6.5, $CH_2\underline{CH_2}O$), 4.53 (2H, s, $NCH_2$), 6.85 (1H, s, isoxazole), 7.26-7.31 (5H, m, Ph), 7.70 (2H, s, H3, H5) ppm.

Example 2

5-(3-{2,6-dimethyl-4-[5-(trifluoromethyl)-1,2,4-oxadiazol-3-yl]phenoxy}propyl)-N-methylisoxazole-3-carboxamide (Compound 2)

Yield 67%. Mp. 121-3° C. Mass (EI), m/z ($I_{relat.}$(%)) 424.3739 $[M]^+$ (78). $C_{19}H_{19}F_3N_4O_4$.

$^1H$ NMR (300 MHz, DMSO-$d_6$): δ 2.13 (2H, dt, J=6.5, 7.7, $CH_2\underline{CH_2}CH_2$), 2.30 (6H, s, $ArCH_3$), 2.70 (3H, d, J=4, $NCH_3$), 3.12 (2H, t, J=7.7, $CH_2Ar$), 3.82 (2H, t, J=6.5, $CH_2\underline{CH_2}O$), 6.70 (1H, s, isoxazole), 7.70 (2H, s, H3, H5), 8.6 (1H, br.d, J=4.0, NH) ppm.

Example 3

5-(3-{2,6-dimethyl-4-[5-(trifluoromethyl)-1,2,4-oxadiazol-3-yl]phenoxy}propyl)isoxazole-3-carboxamide (Compound 3)

Yield 37%. Mp. 147-9° C. Mass (EI), m/z ($I_{relat.}$(%)): 410.3473 $[M]^+$ (67). $C_{19}H_{19}F_3N_4O_4$.

$^1H$ NMR (300 MHz, DMSO-$d_6$): δ 2.23 (2H, dt, J=6.5, 7.7, $CH_2\underline{CH_2}CH_2$), 2.30 (6H, s, $ArCH_3$), 3.12 (2H, t, J=7.7, $CH_2Ar$), 3.80 (2H, t, J=6.5, $CH_2\underline{CH_2}O$), 6.62 (1H, s, isoxazole), 7.70 (3H, m, H3, H5, NH), 8.07 (1H, br.s, NH) ppm.

Example 4

5-(3-{2,6-dimethyl-4-[5-(trifluoromethyl)-1,2,4-oxadiazol-3-yl]phenoxy}propyl)-N,N-dimethyl-isoxazole-3-carboxamide (Compound 4)

Yield 45%. Mp. 78-81° C. Mass (EI), m/z ($I_{relat.}$(%)): 438.4005 $[M]^+$ (81). $C_{20}H_{21}F_3N_4O_4$.

$^1H$ NMR (300 MHz, DMSO-$d_6$): δ 2.13 (2H, dt, J=6.5, 7.6, $CH_2\underline{CH_2}CH_2$), 2.30 (6H, s, $ArCH_3$), 2.90 (3H, s, $NCH_3$), 3.05 (3H, s, $NCH_3$), 3.14 (2H, t, J=7.6, $CH_2Ar$), 3.92 (2H, t, J=6.5, $CH_2\underline{CH_2}O$), 6.55 (1H, s, isoxazole), 7.70 (2H, s, H3, H5) ppm.

Example 5

5-(3-{2,6-dimethyl-4-[5-(trifluoromethyl)-1,2,4-oxadiazol-3-yl]phenoxy}propyl)-N,N-dimethyl-isoxazole-3-carboxamide (Compound 5)

Yield 47%. Mp. 110-2° C. Mass (EI), m/z ($I_{relat.}$(%)): 438.4007 $[M]^+$ (59). $C_{20}H_{21}F_3N_4O_4$.

$^1H$ NMR (300 MHz, DMSO-$d_6$): δ 1.22 (3H, t, J=7.1, $\underline{CH_3}CH_2$), 2.13 (2H, dt, J 25=6.5, 7.6, $CH_2\underline{CH_2}CH_2$), 2.30 (6H, s, $ArCH_3$), 3.10 (2H, q, J=7.1, $CH_3\underline{CH_2}N$), 3.14 (2H, t, J=7.6, $CH_2Ar$), 3.92 (2H, t, J=6.5, $CH_2CH_2O$), 6.83 (1H, s, isoxazole), 7.70 (2H, s, H3, H5) ppm.

Example 6

5-(3-{2-methoxy-4-[5-(trifluoromethyl)-1,2,4-oxadiazol-3-yl]phenoxy}propyl)-N,N-dimethylisoxazole-3-carboxamide (Compound 6)

Yield 34%. Mp. 92-4° C. Mass (EI), m/z ($I_{relat.}$(%)): 440.3733 $[M]^+$ (94). $C_{19}H_{19}F_3N_4O_5$.

$^1H$ NMR (300 MHz, DMSO-$d_6$): δ2.18 (2H, dt, J=6.5, 7.6, $CH_2CH_2CH_2$), 2.98 (3H, s, $NCH_3$), 3.00 (2H, t, J=7.6, $CH_2Ar$), 3.11 (3H, s, $NCH_3$), 3.85 (3H, s, OMe), 4.20 (2H, t, J=6.5, $CH_2CH_2O$), 6.50 (1H, s, isoxazole), 7.23 (1H, d, J=8.8, H6), 7.51 (1H, d, J=1.5, $H_3$), 7.72 (1H, dd, J=1.5, 8.8, H-5) ppm.

Example 7

N,N-dimethyl-5-(3-{2-nitro-4-[5-(trifluoromethyl)-1,2,4-oxadiazol-3-yl]phenoxy}propyl)isoxazole-3-carboxamide (Compound 7)

Yield 59%. Mp. 62-4° C. Mass (EI), m/z ($I_{relat.}$(%)): 455.3449 $[M]^+$ (52). $C_{18}H_{16}F_3N_5O_6$.

$^1H$ NMR (300 MHz, DMSO-$d_6$): δ2.20 (2H, dt, J=6.5, 7.6, $CH_2CH_2CH_2$), 2.98 (3H, s, $NCH_3$), 3.00 (2H, t, J=7.6, $CH_2Ar$), 3.05 (3H, s, $NCH_3$), 4.40 (2H, t, J=6.5, $CH_2CH_2O$), 6.51 (1H, s, isoxazole), 7.55 (1H, d, J=8.8, H6), 8.27 (1H, dd, J=1.5, 8.8, H5), 8.50 (1H, d, J=1.5, H3) ppm.

Example 8

N,N-dimethyl-5-(3-{2-methyl-4-[5-(trifluoromethyl)-1,2,4-oxadiazol-3-yl]phenoxy}propyl)isoxazole-3-carboxamide (Compound 8)

Yield 41%. Mp. 88-89° C. Mass (EI), m/z ($I_{relat.}$(%)): 424.3739 $[M]^+$ (37). $C_{19}H_{19}F_3N_4O_4$.

$^1H$ NMR (300 MHz, DMSO-$d_6$): δ 2.22 (2H, dt, J=6.5, 7.6, $CH_2CH_2CH_2$), 2.24 (3H, s, $ArCH_3$), 3.00 (3H, s, $NCH_3$), 3.05 (2H, t, J=7.6, $CH_2Ar$), 3.10 (3H, s, $NCH_3$), 4.20 (2H, t, J=6.5, $CH_2CH_2O$), 6.50 (1H, s, isoxazole), 7.20 (1H, d, J=8.8, H6), 7.80 (1H, d, J=1.5, H5), 7.81 (1H, dd, J=1.5, 8.8, H3) ppm.

Example 9

5-(3-{2-fluoro-4-[5-(trifluoromethyl)-1,2,4-oxadiazol-3-yl]phenoxy}propyl)-N,N-dimethylisoxazole-3-carboxamide (Compound 9)

Yield 52%. Mp. 83-5° C. Mass (EI), m/z ($I_{relat.}$(%)): 428.3378 $[M]^+$ (29). $C_{18}H_{16}F_4N_4O_4$.

$^1H$ NMR (300 MHz, DMSO-$d_6$): δ 2.21 (2H, dt, J=6.5, 7.6, $CH_2CH_2CH_2$), 2.99 (3H, s, $NCH_3$), 3.10 (3H, s, $NCH_3$), 3.05 (2H, t, J=7.6, $CH_2Ar$), 4.25 (2H, t, J=6.5, $CH_2CH_2O$), 6.52 (1H, s, isoxazole), 7.40 (1H, t, J=8.3, H3), 7.80-7.90 (2H, m, H5, H6) ppm.

Example 10

5-(3-{2-methoxy-6-nitro-4-[5-(trifluoromethyl)-1,2,4-oxadiazol-3-yl]phenoxy}propyl)-N,N-dimethylisoxazole-3-carboxamide (Compound 10)

Yield 58%. Mp. 76-8° C. Mass (EI), m/z ($I_{relat.}$(%)): 485.3709 $[M]^+$ (49). $C_{19}H_{18}F_3N_5O_7$.

$^1H$ NMR (300 MHz, DMSO-$d_6$): δ 2.13 (2H, dt, J=6.5, 7.6, $CH_2CH_2CH_2$), 3.00 (3H, s, $NCH_3$), 3.02 (2H, t, J=7.6, $CH_2Ar$), 3.10 (3H, s, $NCH_3$), 4.00 (3H, s, OMe), 4.25 (2H, t, J=6.5, $CH_2CH_2O$), 6.49 (1H, s, isoxazole), 7.80 (1H, d, J=2.0, H6), 8.07 (1H, d, J=2.0, H4) ppm.

Example 11

N,N-dimethyl-5-(3-{4-[5-(trifluoromethyl)-1,2,4-oxadiazol-3-yl]phenoxy}propyl)isoxazole-3-carboxamide (Compound 11)

Yield 64%. Mp. 95-8° C. Mass (EI), m/z ($I_{relat.}$(%)): 410.3473 $[M]^+$ (39). $C_{18}H_{17}F_3N_4O_4$.

$^1H$ NMR (300 MHz, DMSO-$d_6$): δ 2.15 (2H, dt, J=6.5, 7.6, $CH_2CH_2CH_2$), 2.95 (3H, s, $NCH_3$), 3.00 (2H, t, J=7.6, $CH_2Ar$), 3.11 (3H, s, $NCH_3$), 4.20 (3H, s, OMe), 3.92 (2H, t, J=6.5, $CH_2CH_2O$), 6.50 (1H, s, isoxazole), 7.20 (2H, d, J=7.50, H2, H6), 8.00 (2H, d, J=7.5, H3, H5) ppm.

Example 12

N,N-dimethyl-5-(3-{2-(trifluoromethyl)-4-[5-(trifluoromethyl)-1,2,4-oxadiazol-3-yl]phenoxy}propyl) isoxazole-3-carboxamide (Compound 12)

Yield 74%. Mp. 160-2° C. Mass (EI), m/z ($I_{relat.}$(%)): 478.3453 $[M]^+$ (68). $C_{19}H_{16}F_6N_4O_4$.

$^1H$ NMR (300 MHz, DMSO-$d_6$): δ 2.17 (2H, dt, J=6.5, 7.6, $CH_2CH_2CH_2$), 2.95 (3H, s, $NCH_3$), 3.00 (2H, t, J=7.6, $CH_2Ar$), 3.10 (3H, s, $NCH_3$), 4.22 (2H, t, J=6.5, $CH_2CH_2O$), 6.50 (1H, s, isoxazole), 7.25 (1H, d, J=8.0, H6), 7.85-7.95 (2H, m, H5, H6) ppm.

Example 13

N-methyl-5-(3-{2-(trifluoromethyl)-4-[5-(trifluoromethyl)-1,2,4-oxadiazol-3-yl]phenoxy}propyl) isoxazole-3-carboxamide (Compound 13)

Yield 48%. Mp102-4° C. Mass (EI), m/z (/relat.(%)) 464.3187 $[M]^+$ (73). $C_{18}H_{14}F_6N_4O_4$.

$^1H$ NMR (300 MHz, DMSO-$d_6$): δ 2.17 (2H, dt, J=6.5, 7.6, $CH_2CH_2CH_2$), 2.77 (3H, d, J=2.4, $NCH_3$), 3.05 (2H, t, J=7.6, $CH_2Ar$), 4.30 (2H, t, J=6.5, $CH_2CH_2O$), 6.60 (1H, s, isoxazole), 7.51 (1H, d, J=8.0, H6), 8.24 (1H, s, H3), 8.32 (d, 1H, J=8.0, H5), 8.61 (1H, br.s, NH) ppm.

Example 14

Cytotoxicity

HeLa cells were grown in Eagle minimal essential medium (MEM) supplemented with 10% neonatal calf serum (NCS). The medium used in cytotoxicity tests ("test medium") contained 2% NCS.

The 50% cytotoxic concentrations ($CC_{50}$) are presented in Table 1, below.

Example 15

Determination of In Vitro Antiviral Activity

The CVB3 used in antiviral studies were the pleconaril-sensitive clinical isolate coxsackievirus B3 97927 (CVB3 97927; National Reference Laboratory for Polio- and Enteroviruses at the Robert Koch Institute, Berlin, Germany) as well as 3 pleconaril-resistant variants thereof (CVB3 97927-I1207K, -I1207M, and -I1207T; Braun H. et al. Antiviral Res., 2015, 123, 138). Guanidine HCl was used as positive control in antiviral studies with CVB3. In addition, the anti-rhinovirus activity was studied exemplarily with rhinovirus A2 (RV-A2), rhinovirus B5 (RV-B5) and rhinovirus B14 (RV-B14). Pleconaril (RV-A2 and RV-B14) and RE-2-5c (RV-B5) were included as controls.

CVB3 and RV stocks were prepared in confluent or semi confluent monolayers of HeLa cells propagated with "test medium"), respectively. Viral titers were determined on HeLa cell monolayers by end-point titration. Aliquots were stored at −20° C. until use.

The antiviral activity of pleconaril and its derivatives against the CVB3 97927 and the three variants thereof, and RVs was determined on confluent (CVB3) or semi confluent (RVs) HeLa cells using a cytopathic effect (CPE)-inhibitory assay described previously (Schmidtke M., Schnittler U., Jahn B. et al. J Virol Methods. 2001, 95, 133 and Makarov V. A. et al. Chem Med Chem. 2015. 10, 1629-1634). Briefly, 1-day-old semi confluent (RVs) or 2-day-old confluent (CVB3 97927 and the 3 pleconaril-resistant variants thereof) HeLa cell monolayers growing in 96-well flat-bottomed microtiter plates (Falcon 3075) were treated with 50 μL of half-log compound dilutions and challenged with 50 μL of virus suspension containing a certain multiplicity of infection (moi) that guarantees a complete cytopathic effect (CPE) after 48 hours (CVB3 97927 and the 3 pleconaril-resistant variants thereof) or 72 hours (RVs) after virus challenge. Six wells of non-infected and six wells of infected cells without the test compound served as cell and virus control, respectively, on each plate. Using a crystal violet uptake assay, the inhibition of viral CPE was scored when untreated infected control cells showed maximum cytopathic effect. The 50% inhibitory concentration ($IC_{50}$) of pleconaril derivatives was determined by linear regression. Mean $IC_{50}$ values of at least three separate experiments were calculated by Microsoft Excel (Microsoft Corporation, Redmond, Wash., United States of America). The data are summarized in Table 1, below.

Example 16

Pharmacokinetic Study

The pharmacokinetics of the compound 8 has been studied in white BALB/c male mice. 22 animals with average body weight of 20 g were selected for the study. Before the experiment the animals were kept on standard vivarium ration with dry pelleted feed. All the test animals had free access to water but were deprived of food for 1 hour before administration of the compound. This regimen was continued for another hour after the administration.

Compound was dosed at 100 mg/kg of body weight administered as 0.5 ml of prepared suspension in 0.5% CMC with one drop Tween-80 by intragastric intubation.

The animals were euthanized by decapitation for blood sampling. Blood and brain samples (3 animals per time point) were taken at 0.5, 1, 2, 3, and 7 h after administration for pharmacokinetic evaluation. Blood was collected in heparinized tubes and centrifuged at 3500 RPM. Plasma was separated from formed elements and immediately frozen at −20° C. in freezer. This storage continued before transferring of plasma for analysis. Serum from 6 untreated animals was used as control and for equipment calibration with compound. Mice brain was immediately frozen at −120° C.

Plasma separation: Samples of experimental blood (2.5 mL) from animals were centrifuged at 3500 rpm for 15 minutes.

Sample preparation: A mixture of 50 μL of plasma and 150 μL of MeCN by intensive shaking (Vortex) for 30 sec. Centrifugation 14000 g for 4 min. After centrifugation the 150 μL of organic layer was injected into the HPLC column.

Concentration of experimental compound 8 in mice plasma in ng/ml presented in Table 2, below. See also FIG. 1.

TABLE 1

Comparing Guanidine HCl (Gua-HCl), pleconaril and pleconaril derivatives for inhibition of CVB3 97927 (I1207 and I1092), CVB3 97927 variants and rhinoviruses.

| | | IC50 (μM) against: CVB3 97927 | | | | IC50 (μM) against: Rhinoviruses (RV) | | |
|---|---|---|---|---|---|---|---|---|
| Compound | CC50 (μM) | I1207, I1092 | I1207K, I1092 | I1207M, I1092 | I1207T, I1092 | RV-A2 | RV-B5 | RV-B14 |
| Gua- HCl | n.t. | 711.46 | 704.93 | 724.75 | 806.52 | n.t. | n.t. | n.t. |
| Pleconaril | 45.18 | 0.04 | n.a. | 4.50 | 9.41 | 0.04 | n.a. | 0.06 |
| 1 | >100 | 1.40 | n.a. | 13.08 | n.a. | 0.23 | n.t. | 0.25 |
| 2 | >100 | 0.06 | n.a. | 0.37 | n.a | 0.21 | n.t. | 0.02 |
| 3 | >100 | 0.07 | n.a. | 1.69 | n.a. | 0.50 | n.t. | 0.22 |
| 4 | 13.20 | 0.02 | 8.52 | <0.03 | 1.01 | 0.12 | n.t. | 0.12 |
| 5 | >100 | 0.05 | n.a. | 0.48 | n.a. | 0.60 | n.t. | 0.17 |
| 6 | 68.00 | 0.030 | 51.71 | 0.60 | 1.66 | 1.97 | 3.28 | 0.04 |
| 7 | 22.48 | 0.003 | 6.46 | 0.001 | 0.03 | 0.67 | 7.63 | 0.28 |
| 8 | 13.38 | 0.001 | 3.67 | 0.004 | 0.01 | 0.41 | 2.26 | 0.07 |
| 9 | 20.16 | 0.019 | n.a. | 0.05 | 1.43 | 3.77 | 4.04 | 0.05 |
| 10 | 25.55 | 0.365 | n.a. | 0.88 | 0.84 | 0.32 | n.a. | 0.20 |
| 11 | 27.98 | 07 | 27.49 | 0.02 | 8.11 | 4.61 | 1.74 | 0.04 |
| 12 | 19.23 | 0.16 | 7.18 | 0.16 | 0.53 | 0.32 | n.a. | 6.76 |
| 13 | >100 | 0.02 | n.a. | 0.06 | 1.04 | 0.96 | n.a. | n.a |

n.t. not tested;
n.a. not active

TABLE 2

| Concentration of the compound 8 (ng/ml) in mice plasma. | | | | | | |
|---|---|---|---|---|---|---|
| | Time points after injection, hours | | | | | |
| mice | 0.50 | 1 | 2 | 3 | 5 | 7 |
| 1 | 2031.52 | 1099.04 | 633.79 | 344.86 | 228.15 | 90.82 |
| 2 | 1979.28 | 660.65 | 667.90 | 107.10 | 74.82 | 44.49 |
| 3 | 2114.06 | 1138.34 | 379.89 | 403.55 | 147.00 | 13.49 |
| 4 | 1464.12 | * | 461.99 | * | * | 45.70 |
| 5 | 963.29 | * | * | * | * | * |
| Average | 1710.46 | 966.01 | 535.89 | 285.17 | 123.92 | 49.60 |

* = not determined

Pharmacokinetic parameters were calculated with the ESTRIP computer program using model-independent method and presented in Table 3, below. Compound 8 was found to have a very high oral bioavailability.

TABLE 3

| Pharmacokinetic parameters of compound 8. | |
|---|---|
| Parameter | |
| $AUC_{0-\infty}$, ng/mL*h | 3015.5 |
| $C_{max.}$, ng/mL | 1710.5 ± 489.2 |
| $T_{max.}$, h | 0.5 |
| CL, l/h | 0.66 |
| $k_{el}$, 1/h | 0.4373 |
| $T_{1/2}$, h | 1.58 |
| MRT, h | 2.15 |
| Vd, L | 1.52 |

(maximum concentration (Cmax)—maximal measured value; time to maximum concentration (Tmax)—time of measuring of maximum concentration; area under pharmacokinetic curve (AUCo-t) - within observation period (12 hours); calculated using trapezium method; area under pharmacokinetic curve (AUCo-∞)— from time zero to infinity; half-life (T½)—calculated using equation ln2/$k_{el}$; mean drug retention time in systemic bloodstream (MRT); relative absorption speed Cmax/AUC o-t; elimination constant—$k_{el}$; volume of distribution—Vd; total clearance—Cl.)

Example 17

CYP Induction

As CYP3A4 induction is a key issue for pleconaril failure in the clinic, compound 8 was tested in cryopreserved hepatocytes (BioIVT, Westbury, N.Y., United States of America) (1, 10, 100 μM) using rifampicin as positive control and midazolam as the substrate for the enzyme (Lu, C.; Li, A. P. *Chem Biol Interact* 2001,134, (3), 271-81). At 10 μM pleconaril induction was 2.7× (30% of control) vs compound 8 1.4× (7% of control) and positive control 10 μM Rifampicin 6.6λ. At 1 μM pleconaril resulted in 1.7× induction (13% of control) vs compound 8 1.2× (3% of control). These results demonstrate compound 8 is far less likely to represent a CYP3A4 induction risk compared with pleconaril, which is a major differentiating factor which will impact clinical use. When pleconaril and compound 8 are tested for binding to the receptor PXR using a competitive binding assay sold under the tradename LANTHASCREEN™ TR-FRET competitive binding assay (Life Technologies Corporation, Carlsbad, Calif., United States of America), their $IC_{50}$'s were >100 μM (SR-12813 was used as a positive control). This suggests these compounds do not induce CYP3A4 activity via PXR.

Example 18

SOS Chromotest

*Escherichia coli* PQ37 was developed by Quillardet and Hofnung 1993 from *E. coli* K-12 by means of a sfiA::lacZ operon fusion in which the β-galactosidase gene lacZ is placed under the control of sfiA, one of the SOS genes. In addition to this operon fusion, there is a deletion in the lac region so that the activity of β-galactosidase is entirely dependent upon the expression of sfiA. The construction of this bacterial strain is described by Quillardet and Hofnung (Quillardet P., Hofnung M. Mutat Res. 1993, 297, 3, 235).

*Escherichia coli* PQ37 strain was grown overnight at 37° C., with shaking, in Luria Broth Base supplemented with 50 pg/mL Ampicillin. Bacteria were grown to mid-logarithmic phase and adjusted to an optical density of 0.4. The second day, Luria Broth Base supplemented with 1.5% Agar was autoclaved for 15 minutes at 121° C. and then put into a water bath at 55° C. for 1 hour. 80 mL of warm agar was transferred into a plastic bottle (Milian, PETG 2019-0125) supplemented with 50 mg/mL ampicillin and 0.005% X-Gal (dissolved into DMF). 4 mL of *E. coli* PQ37 was added to the mixture and 70 mL of it was transferred into a square petri dish (Grenier, 120×120 mm). Petri dish containing the mixture was dried 15 minutes at RT and once the mixture became solid, 6 mm absorbent disks were stuck on the plate. 5 μL of each compound were added on the disk with a pipetman (Gilson P20, Gilson, Lewis Center, Ohio, United States of America) and the petri dish was incubated overnight at 37° C. The third day, zones of inhibition were recorded with a ruler and a picture of the plate was taken with a scanner (Canon 8800F, Canon USA, Inc., Huntington, N.Y., United States of America). Zone of inhibition was calculated by eye using a ruler and presence/absence of blue halo was reporter.

None of the test compounds appeared to be genotoxic in *E. coli* PQ37 in the SOS-chromotest, at 10 mg/mL. Moreover, no inhibition of *E. coli* growth was detected. See Table 4, below. The positive control, 4NQO, inhibited as expected the growth of *E. coli* PQ37, the zone of inhibition has 25 mm of diameter and the presence of a blue halo was detected indicative that X-Gal was metabolized (DNA damage). The negative control DMSO in this test, does not inhibit the growth of *E. coli* PQ37.

TABLE 4

Mutagenicity of the compounds, DMSO and 4NQO. DMSO was used as negative control. 4NQO was used as positive control. All drugs were tested at 10 mg/mL and DMSO 99%.

| Compound | Concentration | Mutagenicity | Zone of inhibition (mm) |
|---|---|---|---|
| 2 | 10 mg/mL | NO | 0 |
| 4 | 10 mg/mL | NO | 0 |
| 7 | 10 mg/mL | NO | 0 |
| 8 | 10 mg/mL | NO | 0 |
| 12 | 10 mg/mL | NO | 0 |
| 4NQO | 10 mg/mL | YES | 25 |
| DMSO | 99% | NO | 0 |

With regard to the potential mutagenicity of these compounds, results showed that none of them are mutagenic and they are not inhibiting the growth of *Escherichia Coli* bacteria.

Example 19

Additional Antiviral Activity

The antiviral activity of compound 8 for polio virus-1 (strain Mahoney). Enterovirus 68 (strain US/KY/14-18953) and enterovirus 71 (strain Tainan/4643/98). The testing of the polio virus-1 and enterovirus 71 was conducted in vero 76 cells and the testing of enterovirus 68 was conducted in RC cells. In addition, the antiviral activity of compound 8 was tested for influenza A virus, subtype H1N1 (strain California/07/2009) and mouse-adapted EV D68.

Four-concentration CPE inhibition assays were performed on confluent or near-confluent cell culture monolayers in 96-well plates. Cells were maintained in MEM or DMEM supplemented with FBS as required for each cell line. For antiviral assays, the same medium was used but with FBS reduced to 2% or less and supplemented with 50 pg/mL gentamicin (25 mM MgCl for enterovirus-D68). The test compound (i.e., compound 8) was prepared at four final concentrations, usually 0.1, 1.0, 10, and 100 pg/mL or 25 μM. Five microwells were used per dilution: three for infected cultures and two for uninfected toxicity evaluation run in parallel. Controls included six microwells that were infected but not treated (virus controls) and six that were untreated (cell controls). The virus control and cell control wells were on every microplate. A known active drug was tested in parallel with each assay as a positive control, using the same method as is applied for test compounds.

Growth medium was removed from the 96-well plates of cells, then the test compound (compound 8) was applied in 0.1 mL volume to wells at 2× concentration. Virus, normally <100 $CCID_{50}$ (50% cell culture infectious doses) in 0.1 mL volume, was added to wells designated for virus infection. Medium devoid of virus was placed in toxicity control wells and cell control wells. Plates were incubated at 37° C. (33° C. for rhinovirus and enterovirus-D68) with 5% $CO_2$ until maximum CPE was observed microscopically in virus control wells. Plates were then stained with 0.011% neutral red (27, 46, 62) for approximately two hours at 37° C. with 5% $CO_2$. The neutral red medium was removed by complete aspiration, and the cells rinsed with phosphate buffered saline (PBS) to remove residual dye. The PBS was completely removed and the incorporated neutral red was eluted with 50% Sorensen's citrate buffer/50% ethanol for at least 30 minutes. Neutral red dye penetrates into living cells, thus, the more intense the red color, the larger the number of viable cells present. The dye content in each well was quantified by optical density (OD) on a spectrophotometer at 540 nm wavelength. The OD for each set of wells was converted to a percentage compared to untreated control wells using a computer-based spreadsheet. Infected wells were normalized to the virus control. The 50% effective ($EC_{50}$, virus-inhibitory) concentrations and 50% cytotoxic ($CC_{50}$, cell-inhibitory) concentrations were then calculated by regression analysis. The quotient of $CC_{50}$ divided by $EC_{50}$ gives the selectivity index ($SI_{50}$) value. $SI_{50}$ values of ≥ are considered active. The percent CPE in each well can also be read microscopically, calculated as above, and reported as a second data set from the same plate for verification.

Results are summarized in Table 5, below. Enterovirus 68 (EV68) is believed to be associated with acute flaccid myelitis, while enterovirus 71 (EV71) is associated with hand-foot-and-mouth disease. Notably, there are currently no drugs approved for the treatment of acute flaccid myelitis.

TABLE 5

Additional Antiviral Activity of Compound 8.

| Virus | $EC_{50}$ (μM) | $CC_{50}$ (μM) | $SI_{50}$ |
|---|---|---|---|
| Polio virus-1 (Mahoney) | 0.32 | 3.55 | 11 |
| Enterovirus 68 (US/KY/14-18953) | 0.018 | 52 | >520 |
| Enterovirus 71 (Tainan/4643/98) | 0.94 | 23 | 24 |
| H1N1 (Califomia/07/2009) | $EC_{90}$ 4.4 | 19 | 4.3 |
| Mouse adapted EV-D68 | 0.023 | 4 | 173 |

Example 20

The maximum tolerated dose (MTD) of compound 8 was determined by PO route in 4-week-old AG129 mice. Briefly, 20 4-week-old AG129 mice were split into four groups, 1-4. Each group was administered treatment (vehicle for Group 1; 100 mg/kg/d compound 8 for Group 2; 30 mg/kg/d compound 8 for Group 3; or 10 mg/kg/d compound 8 for Group 4) twice daily by mouth for five days. Vehicle for Group 1 was a suspension of 0.5% carboxymethylcellulose (CMC) and 1 drop of Tween-80 in sterile water. Mice were observed daily for body weight and mortality for 14 days.

Maximum tolerated dose (MTD): at least 100 milligrams per kilogram body weight per day (PO) in mice.

In Vitro ADME Data

In vitro ADME studies were performed on compound 8.

Solubility at pH 7.4 is 0.11 μM.

CYP1A2>50 μM, CYP2CP 50 μM, CYP2C19 2.1 μM, CYP2D6>50 μM, CYP3A4>μM

Cell permeability (Caco-2) results were as follows: Apical (A) to (Basolateral) B $8.8\times10^{-4}$ cm/s; B to A $30.9\times10^{-4}$; efflux ratio 3.5. Thus, it appears that compound 8 is a likely P-gp substrate.

Microsomal Stability:

Mouse liver microsomes (MLM): half-life ($t_{1/2}$)=19.6 min; intrinsic clearance ($CL_{int}$): 70.6 μL/min/mg (unstable)

Human liver microsomes (HLM): $t_{1/2}$=55.3 min; $CL_{int}$=25.1 μL/min/mg

Protein binding:

Human: 99.7% bound, 93.9% stability

Mouse: 99.8% bound, 88.1% stability

Maximum tolerated dose (MTD): at least 100 milligrams per kilogram body weight per day (PO) in mice.

Example 21

In Vivo Efficacy Against EVD68

Animals: Four-week-old male and female AG129 mice from a specific-pathogen-free colony were used to determine the efficacy of compound 8 for enterovirus D68 (EVD68). The mice were bred and maintained on irradiated food and autoclaved water.

Compounds: Compound 8 was prepared in 0.5% carboxymethylcellulose (CMC) and 0.5% Tween 20 in sterile water. Guanidine HCl (guanidine) was obtained from Sigma-Aldrich (St. Louis, Mo., United States of America) and served as a positive control at a dose of 100 mg/kg/day. Sterile saline was used as a vehicle for guanidine.

Virus: Enterovirus D68 (strain US/MO/14-18949, NR-49130) was serially passaged 30 times in the lungs of 4-week-old AG129 mice and then plaque-purified three times in Rhabdomyosarcoma (RD) cells obtained from the American Type Culture Collection (ATCC, Manassas, Va., United States of America). The resulting virus stock was amplified twice in RD cells to create a working stock. The virus used for infection was designated EV-D68 mouse passage 30 (MP30), plaque purified (PP).

Experiment design: A total of 65 mice were randomized into 5 groups of 12 mice each and one group of 6 mice (normal controls) as shown in Table 6, below. Mice were treated per os (PO) with compound 8 once daily for 5 days beginning 2 hours pre-infection. Treatment with guanidine started 4 hours post-infection and continued twice daily for 5 days. The placebo (vehicle only) was administered by p.o. once daily for 5 days starting 2 hours pre-virus exposure. Mice were anesthetized by i.p. injection of ketamine (100 mg/kg) and then infected via intranasal (IN) instillation of $1\times10^{4.5}$ $CCID_{50}$ of EV-D68 MP30 PP in a 90 μl volume of MEM. Mice were weighed prior to treatment and then daily thereafter to assess the effects of treatment on ameliorating weight loss due to virus infection. Four mice from each treatment group were euthanized on days 1, 3, and 5 post-infection for evaluation of blood and lung virus titers, and lung cytokine concentrations. In addition, one mouse from the normal controls was euthanized on days 1, 3, and 5 post-infection as a negative control for cytokine analysis.

TABLE 6

Experimental Design for study of Efficacy versus EV-D68.

| Group No. | Infected | Compound | Dosage | Route | Treatment Schedule |
|---|---|---|---|---|---|
| 1 | Yes | Placebo* | — | PO | q.d. x 5 d |
| 2 | Yes | Compound 8 | 100 mg/kg/d | | beginning 2 h |
| 3 | Yes | Compound 8 | 30 mg/kg/d | | pre-infection |
| 4 | Yes | Compound 8 | 10 mg/kg/d | | |
| 5 | Yes | Guanidine | 100 mg/kg/d | IP | b.i.d. x 5 days beginning 4 h post-infection |
| 6 | No | Normal Controls | | | |

*Vehicle: suspension of 0.5% carboxymethylcellulose (CMC) and 0.5% Tween20 in sterile water.

Blood and lung virus titer determination: Viremia was evaluated in whole blood on human rhabdomyosarcoma (RD) cells in microtiter plates, as described previously (Evans et al. Antiviral Research, 2019, 162, 6170; Hurst et al., Virology, 2019, 526, 146-154). In addition, each mouse lung was homogenized in minimal essential media (MEM) solution and assayed for infectious virus in RD cells (Evans et al. Antiviral Research, 2019, 162, 6170; Hurst et al., Virology, 2019, 526, 146-154). Fifty percent cell culture infectious doses ($CCID_{50}$) were converted to $CCID_{50}$ per gram of lung tissue prior to statistical analysis. Virus titer differences were evaluated by analysis of variance (ANOVA) on log-transformed values assuming equal variance and normal distribution. Following ANOVA individual treatment values were compared to placebo control by Tukey's pair-wise comparison test using Prism 8.4.3. (GraphPad Software Inc., San Diego, Calif., United States of America).

Lung cytokine/chemokine determinations: samples (200 μl) from lung homogenates were tested for cytokines and chemokines using a chemiluminescent ELISA-based assay (sold under the tradename Quansys Biosciences Q-PLEX™ Array, Quansys Biosciences, Logan, Utah, United States of America) according to the manufacturer's instructions. The Quansys multiplex ELISA is a quantitative test in which 16 distinct capture antibodies have been applied to each well of a 96-well plate in a defined array. Each sample supernatant was tested at 2 dilutions for the following: IL-1α, IL-1β, IL-2, IL-3, IL-4, IL-5, IL-6, IL-10, IL-12p70, IL-17, MCP-1, IFN-γ, TNFα, MIP-1α, GM-CSF, and RANTES.

Cytokine and chemokine titers are reported in pg/ml of lung lavage fluid. Titer differences were evaluated by ANOVA on values assuming equal variance and normal distribution. In addition, treatment group mean values were evaluated by two-way ANOVA for effects based on the day post-infection using Prism 8.4.3 (GraphPad Software Inc., San Diego, Calif., United States of America).

Statistical analysis: Mean body weights were analyzed by one-way analysis of variance (ANOVA) followed by Tukey's multiple comparison tests using Prism 8.4.3 (GraphPad Software Inc., San Diego, Calif., United States of America). For each day post-infection, lung and blood virus titers from treated groups were compared to lung and blood titers from placebo-treated mice using a one-way analysis of variance (ANOVA) followed by Tukey's pair-wise comparison test. For each cytokine/chemokine, the concentrations from treated mice were compared to placebo-treated mice using a two-way ANOVA for effects based on the day post-infection.

Results: This study determined the efficacy of 11526092 for treatment of an EV-D68 respiratory infection in four-week-old AG129 mice. The EV-D68 respiratory model based on intranasal infection of 4-week-old AG129 mice is a non-lethal model that includes viremia with rapid tissue distribution of virus, including high virus titers in lung tissues and an elevation of proinflammatory cytokines in the lung.

Figure 2:
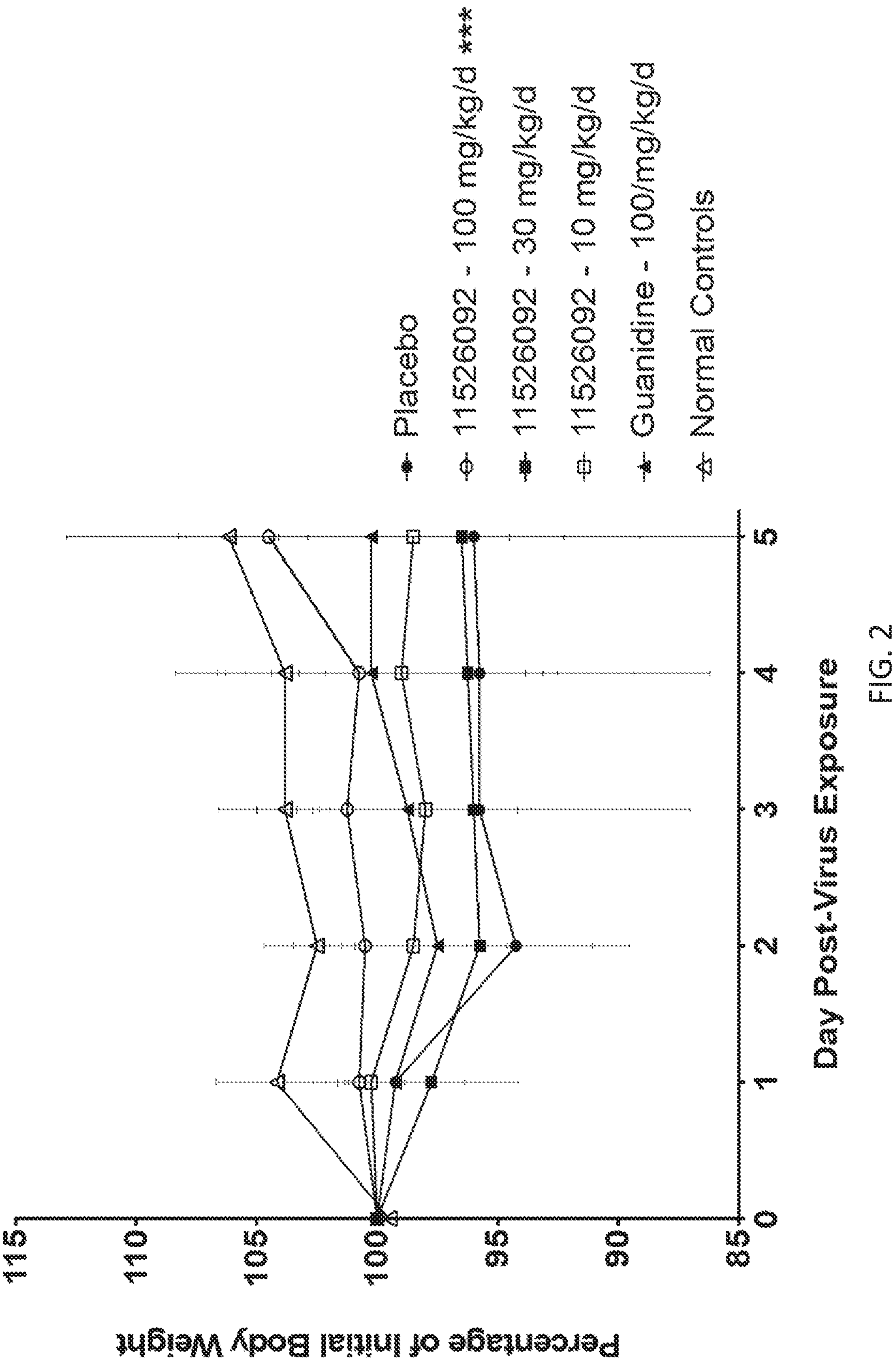
Figure 3A:
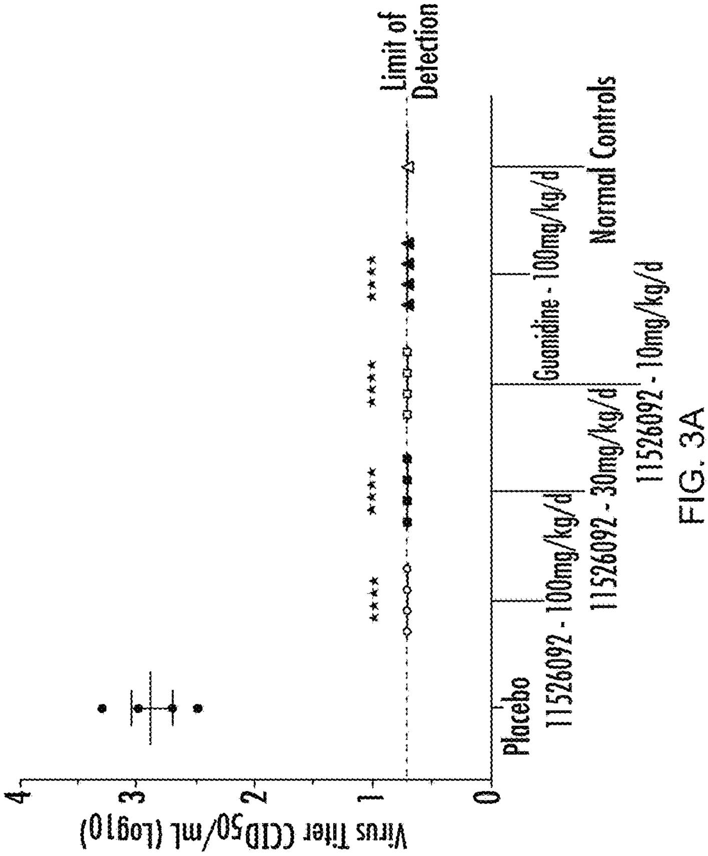
FIGS. 3A-3B: Blood virus titers (measured in 50 percent cell culture infectious dose ($CCID_{50}$) per milliliter (mL) times log 10) from mice following treatment with Compound 8 (also referred to herein as 11526092) at a dose of 10 (unfilled squares), 30 (filled squares), or 100 (unfilled circles) milligrams per kilogram body weight per day (mg/kg/d). For comparison, the blood virus titers of infected mice treated with 100 mg/kg/d guanidine (filled triangles), a placebo (filled circles), and uninfected mice (Normal Controls, unfilled triangles) are also shown.
Figure 3B:
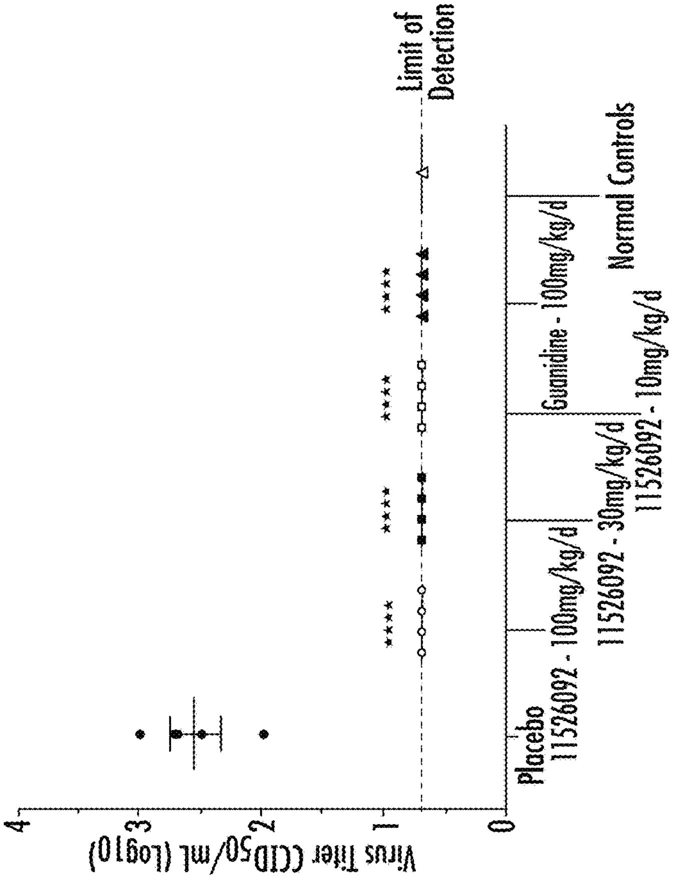

FIG. 2 show loss of weight (percentage of initial body weight) from mice following treatment with compound 8 and EV-D68 infection. Treatment with compound 8 at 100 mg/kg/d provided significant protection from weight loss following infection. All doses of compound 8 were able to reduce viremia on days 1 and 3 post-infection. See FIGS. 3A and 3B. No virus was detected for any group on day 5 post infection.

Figure 4A:
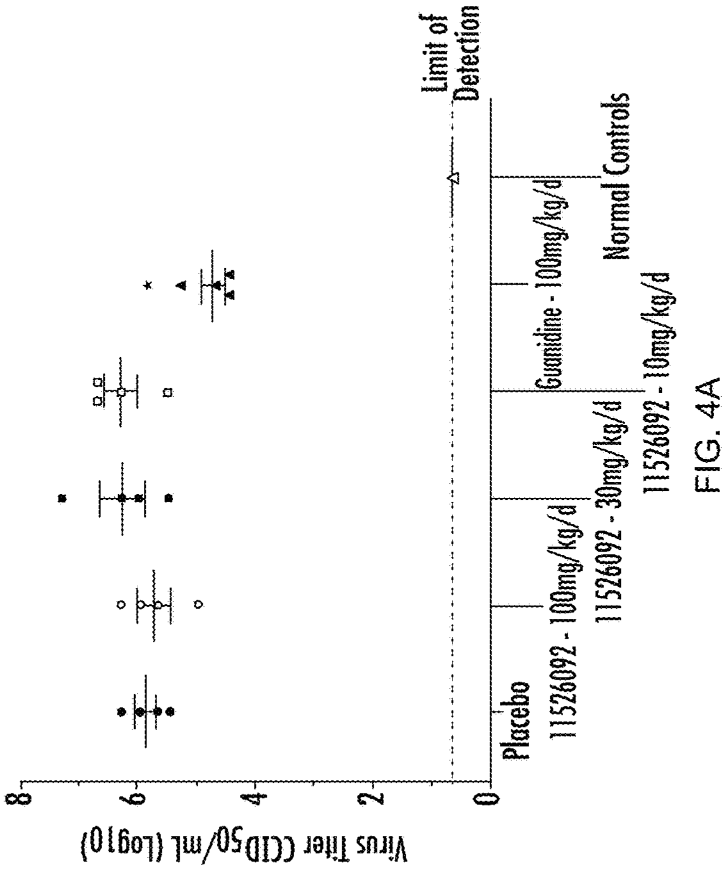
FIGS. 4A-4C: Lung virus titers (measured in 50 percent cell culture infectious dose ($CCID_{50}$) per milliliter (mL) times log 10) from mice following treatment with compound 8 (also referred to as 11526092) at a dose of 10 (unfilled squares), 30 (filled squares), or 100 (unfilled circles) milligrams per kilogram body weight per day (mg/kg/d). For comparison, the lung virus titers of infected mice treated with 100 mg/kg/d guanidine (filled triangles), a placebo (filled circles), and uninfected mice (Normal Controls, unfilled triangles) are also shown.
Figure 4B:
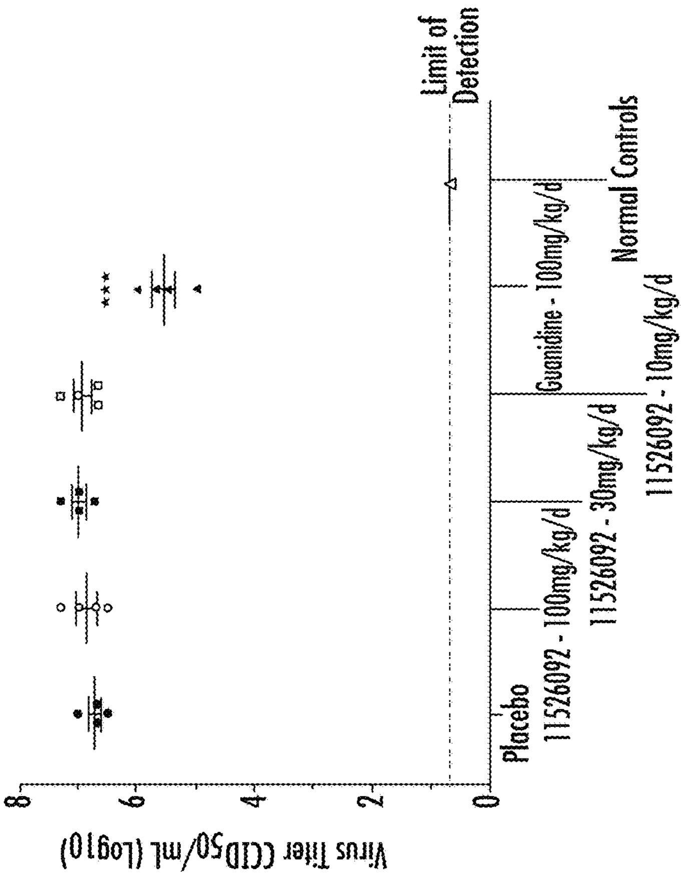
Figure 4C:
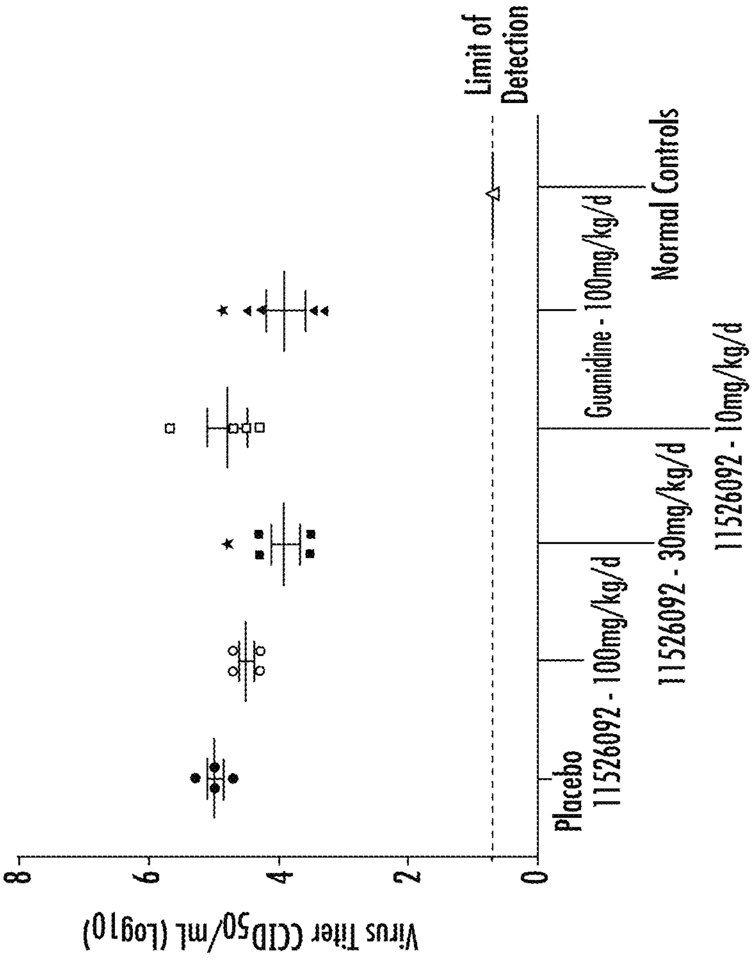
Figure 5B:
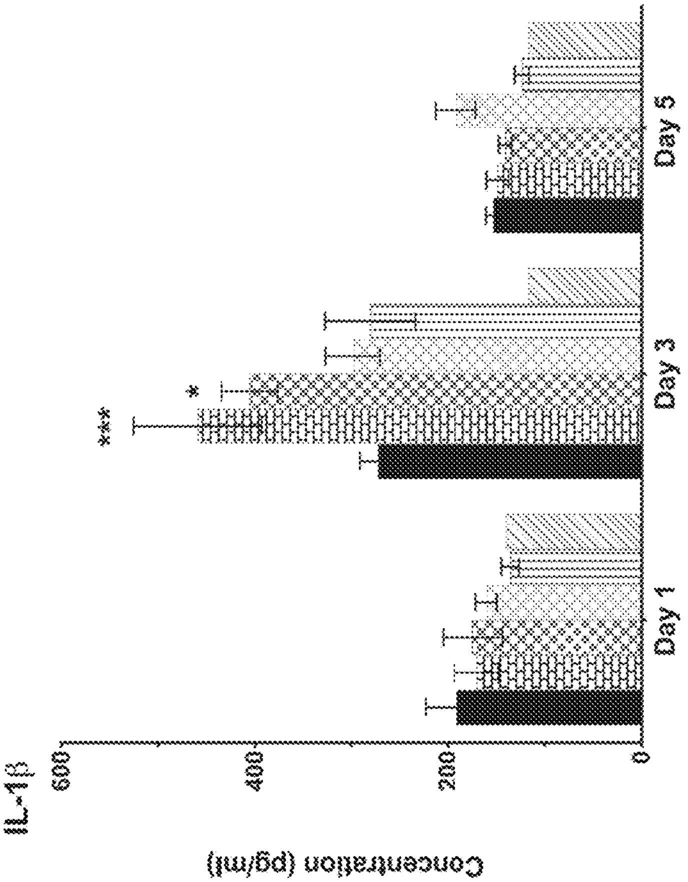
FIGS. 5A-5D: Concentrations (measured in picograms per milliliter (pg/ml) on days 1, 3, and 5 post-infection (p.i.)) of interleukin-1α (IL-1α, FIG. 5A), interleukin-1β (IL-1β, FIG. 5B), interleukin-2 (IL-2, FIG. 5C), and interleukin-3 (IL-3, FIG. 5D) in lung homogenates from mice following enterovirus D68 (EV-D68) infection and treatment with compound 8 (also referred to herein as 11526092) at a dose of 10, 30, or 100 milligrams per kilogram body weight per day (mg/kg/d). For comparison, the same concentrations are shown from infected mice treated with 100 mg/kg/d guanidine, a placebo, and uninfected mice (Normal Controls) are also shown. Treatment with compound 8 at a dose of 30 mg/kg/day increased concentrations of IL-1a (FIG. 5A) and IL-1β(FIG. 5B) on day 3 p.i. compared to placebo-treated mice. In addition, all doses of compound 8 decreased IL-3 on day 1 (FIG. 5D). In each of FIGS. 5A-5D, each set of six data bars is as follows, from left to right: placebo (filled bar), 100 mg/kg/d compound 8 (bar filled with offset rectangles), 30 mg/kg/d compound 8 (bar filled with checkerboard pattern), 10 mg (crosshatched bar), 100 mg/kg/d guanidine (bar filled with vertical lines), normal controls (bar filled with slanted lines). (*P<0.05, P<0.01, *P<0.001).
Figure 5A:
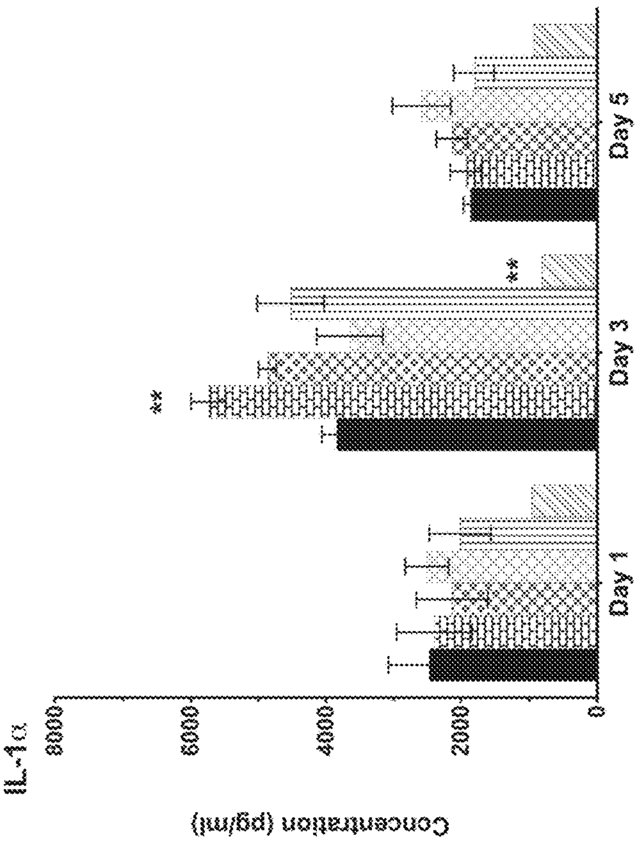
Figure 5D:
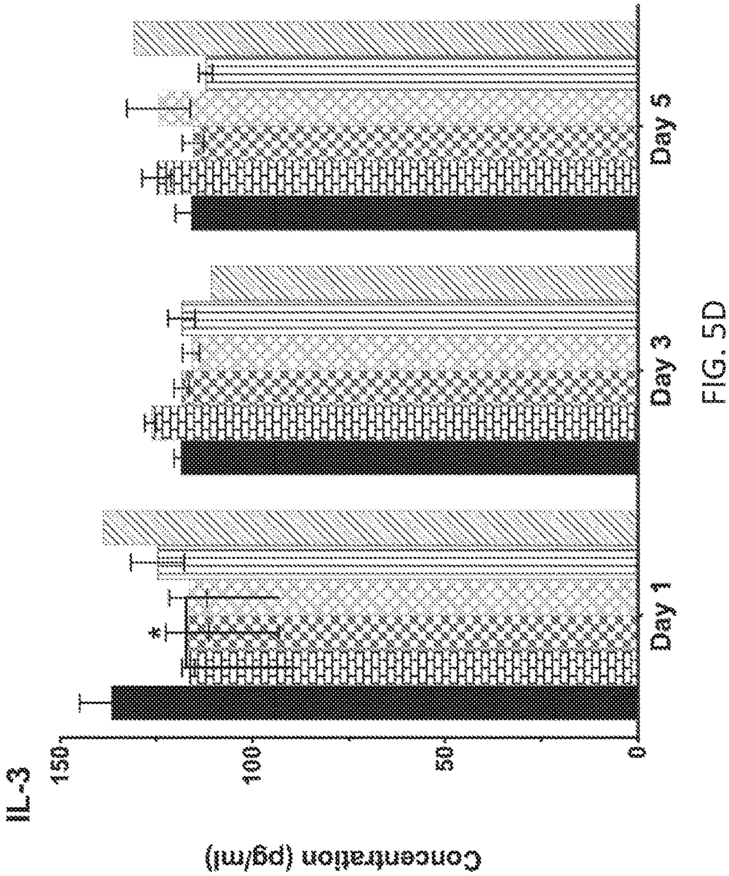
Figure 5C:
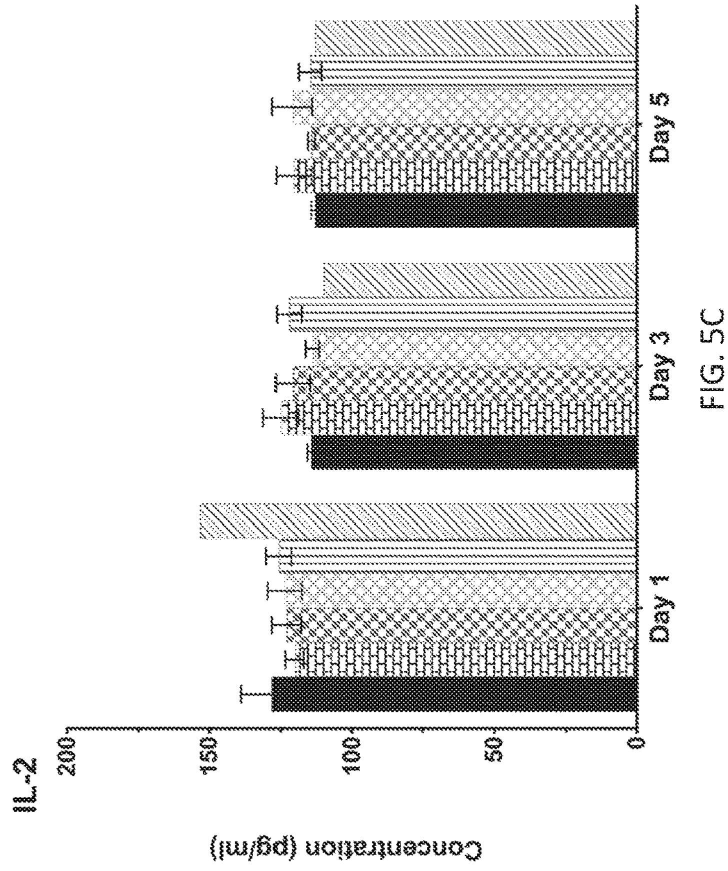
Figure 6B:
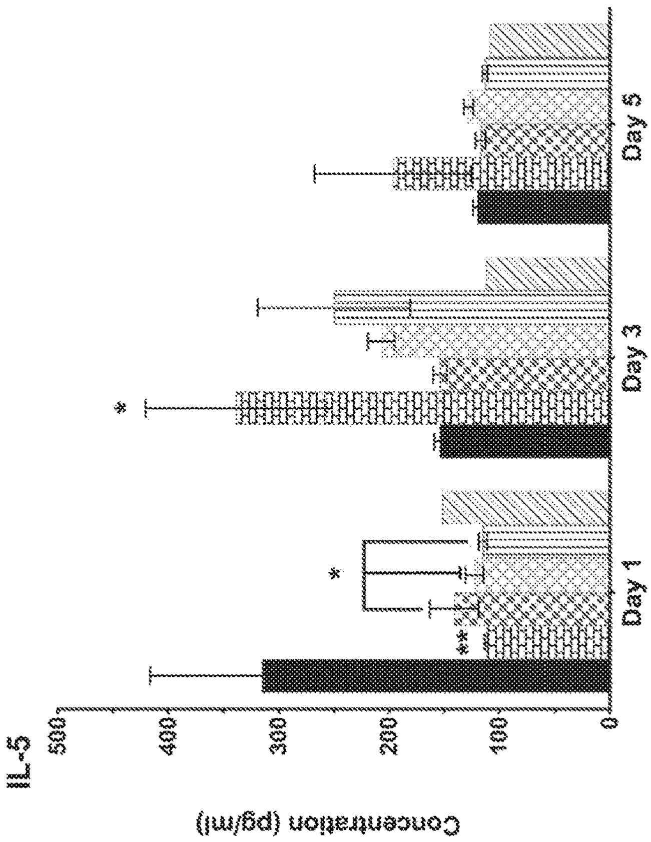
FIG. 6A-6D: Lung concentrations (measured in picograms per milliliter (pg/ml) on days 1, 3, and 5 post-infection (p.i.)) of interleukin-4 (IL-4, FIG. 6A), interleukin-5 (IL-5, FIG. 6B), interleukin-6 (IL-6, FIG. 6C), and interleukin-10 (IL-10, FIG. 6D) in lung homogenates from mice following enterovirus D68 (EV-D68) infection and treatment with compound 8 (also referred to herein as 11526092) at a dose of 10, 30, or 100 milligrams per kilogram body weight per day (mg/kg/d). For comparison, the same concentrations are shown from infected mice treated with 100 mg/kg/d guanidine, a placebo, and uninfected mice (Normal Controls) are also shown. Treatment with compound 8 at a dose of 100 mg/kg/day increased concentrations of IL-4 (FIG. 6A), IL-5 (FIG. 6B), and IL-6 (FIG. 6C) on day 3 p.i. compared to placebo-treated mice. However, the 100 mg dose also decreased IL-5 on day 1 p.i.
Figure 6A:
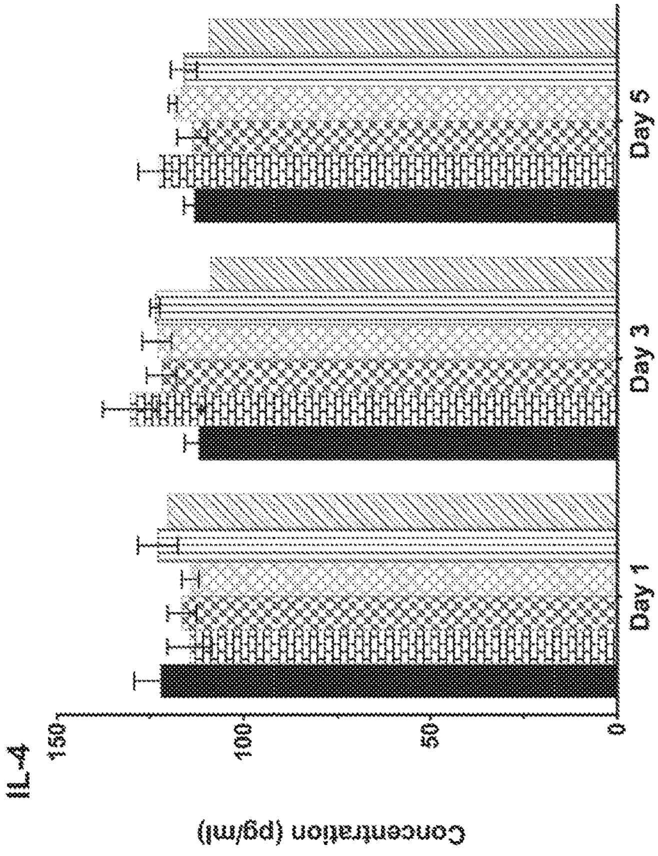
Figure 6D:
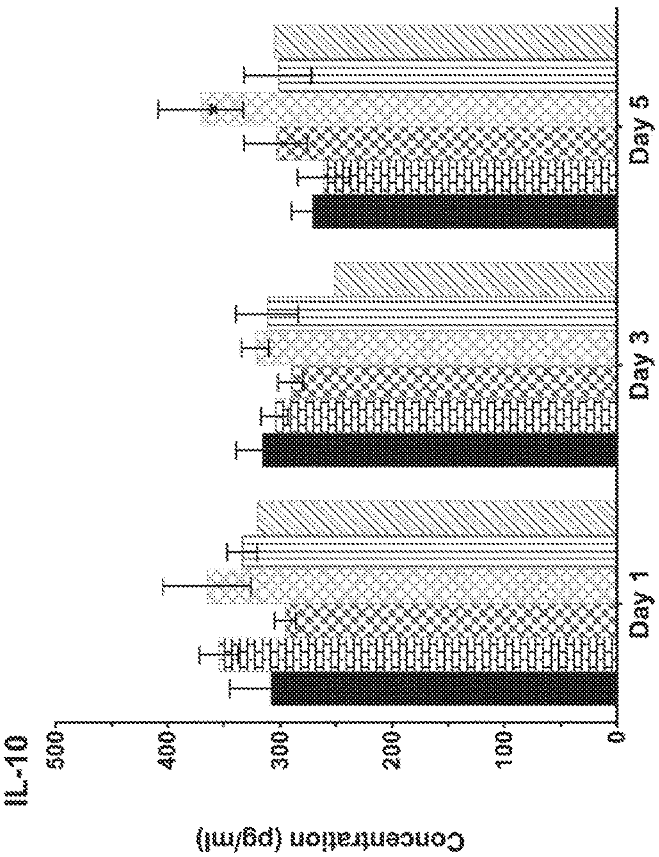
Figure 6C:
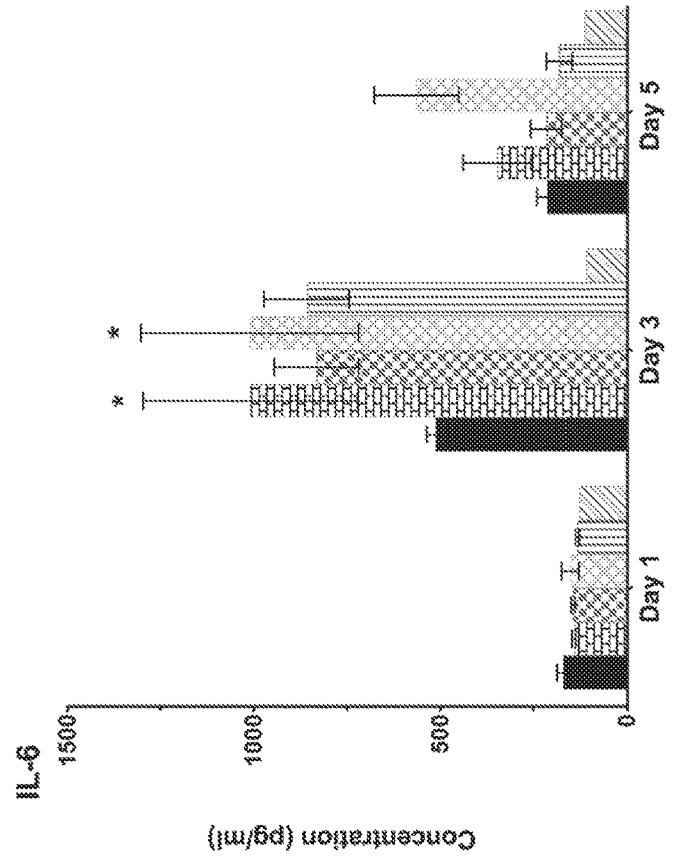
Figure 7B:
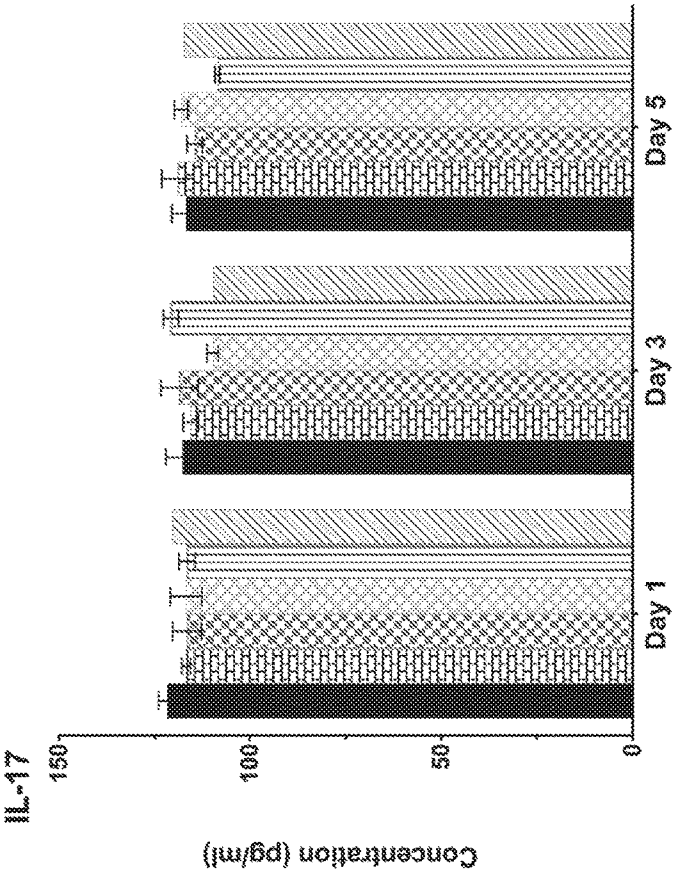
FIGS. 7A-7D: Lung concentrations (measured in picograms per milliliter (pg/ml) on days 1, 3, and 5 post-infection (p.i.)) of interleukin-12p70 (IL-12p70, FIG. 7A), interleukin-17 (IL-17, FIG. 7B), monocyte chemoattractant protein-1 (MCP-1, FIG. 7C) and interferon-gamma (IFNγ, FIG. 7D) in lung homogenates from mice following infection with enterovirus D68 (EV-D68) and treatment with compound 8 (also referred to as 11526092) at a dose of 10, 30, or 100 milligrams per kilogram body weight per day (mg/kg/d). For comparison, the same concentrations are shown from infected mice treated with 100 mg/kg/d guanidine, a placebo, and uninfected mice (Normal Controls) are also shown. Treatment with compound 8 at a dose of 100 mg/kg/day decreased concentrations of MCP-1 on day 1 p.i.
Figure 7A:
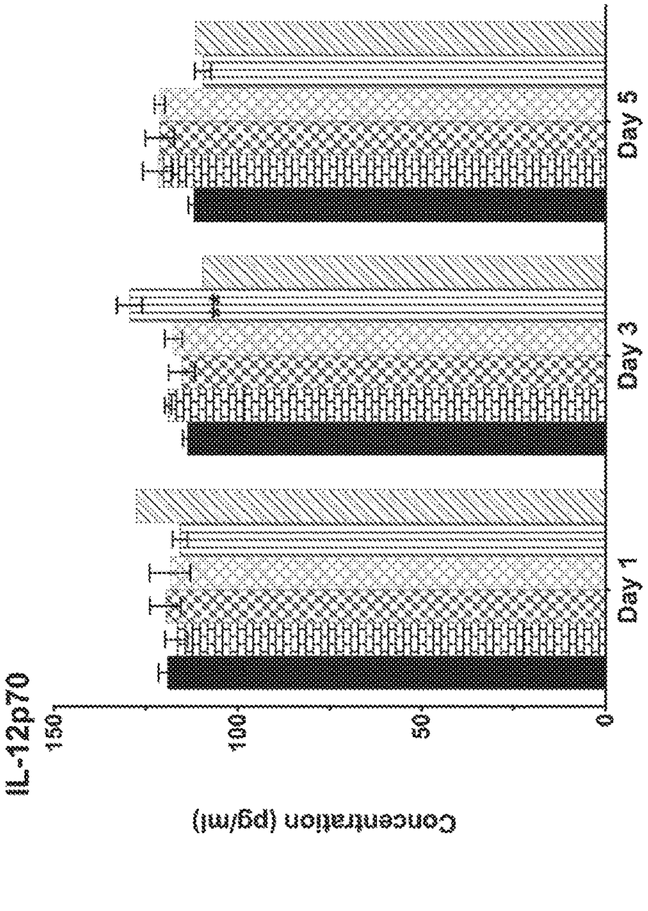
Figure 7D:
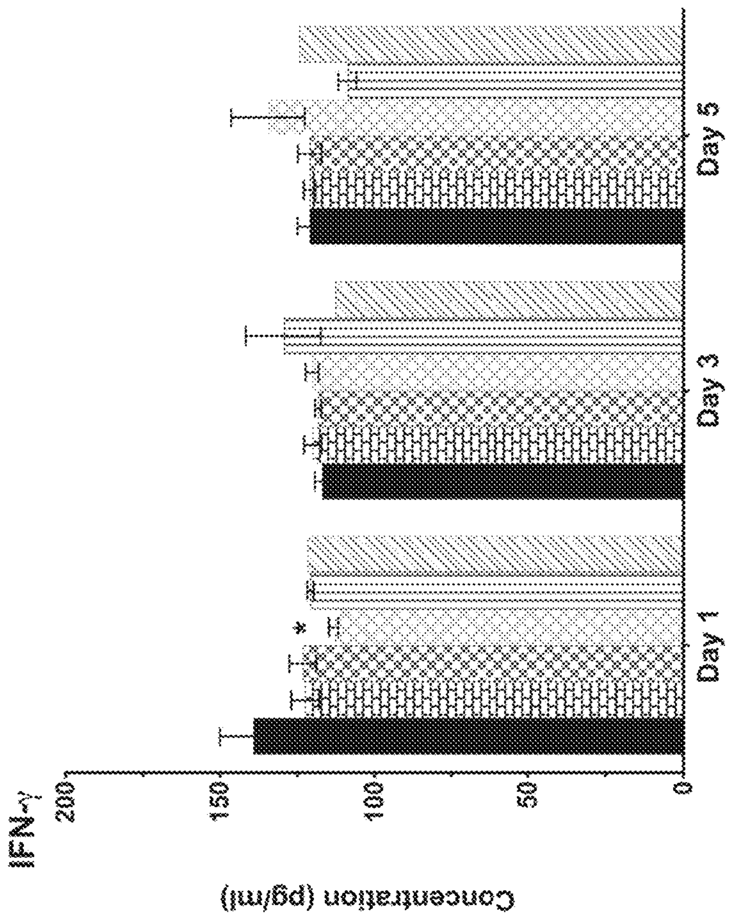
Figure 7C:
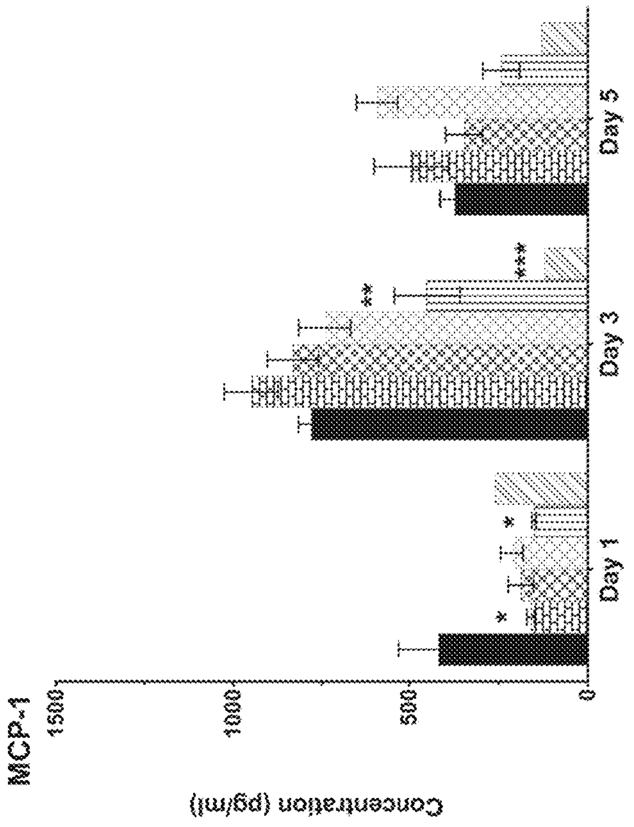
Figure 8A:
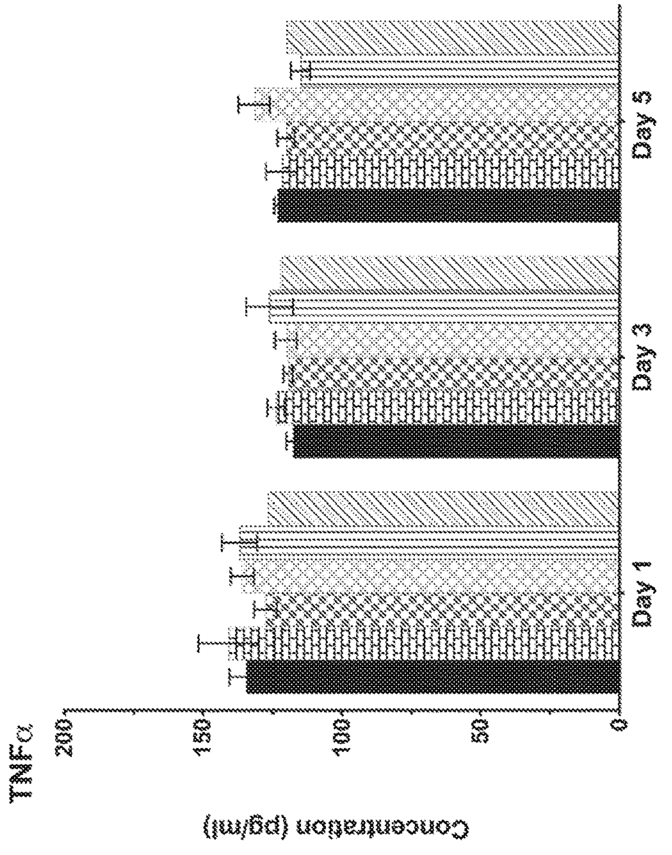
FIGS. 8A-8D: Lung concentrations (measured in picograms per milliliter (pg/ml) on days 1, 3, and 5 post-infection (p.i.)) of tumor necrosis factor-alpha (TNFα, FIG. 8A), macrophage inflammatory factor-1alpha (MIP-1a, FIG. 8B), granulocyte/macrophage colony stimulating factor (GM-CSF, FIG. 8C), and regulated upon activation, normal T cell expressed and secreted (RANTES, FIG. 8D) in lung homogenates from mice following enterovirus D68 (EV-D68) infection and treatment with compound 8 (also referred to as 11526092) at a dose of 10, 30, or 100 milligrams per kilogram body weight per day (mg/kg/d). For comparison, the same concentrations are shown from infected mice treated with 100 mg/kg/d guanidine, a placebo, and uninfected mice (Normal Controls) are also shown. Treatment with compound 8 at a dose of 30 mg/kg/day increased concentrations of MIP-1a on day 5 p.i.
Figure 8B:
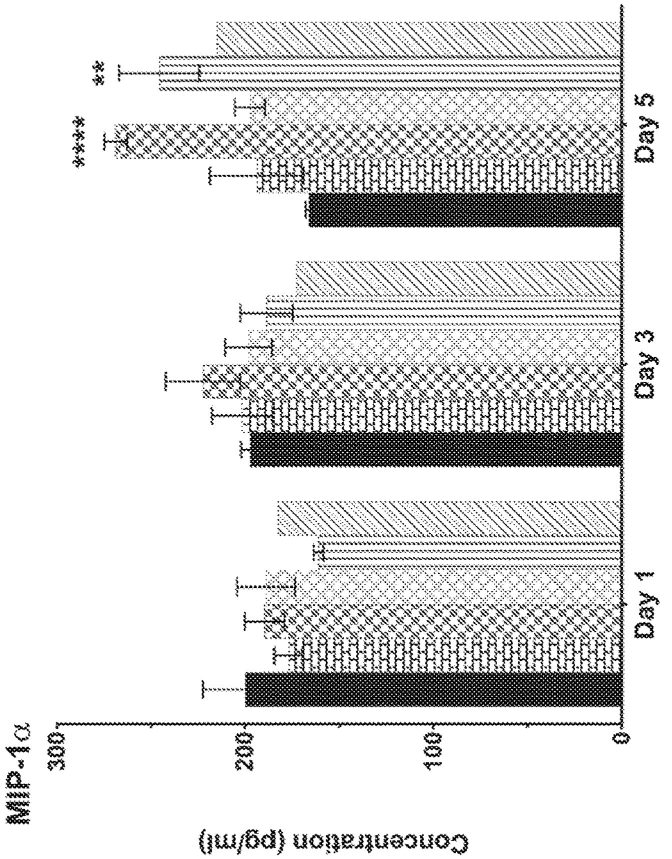
Figure 8D:
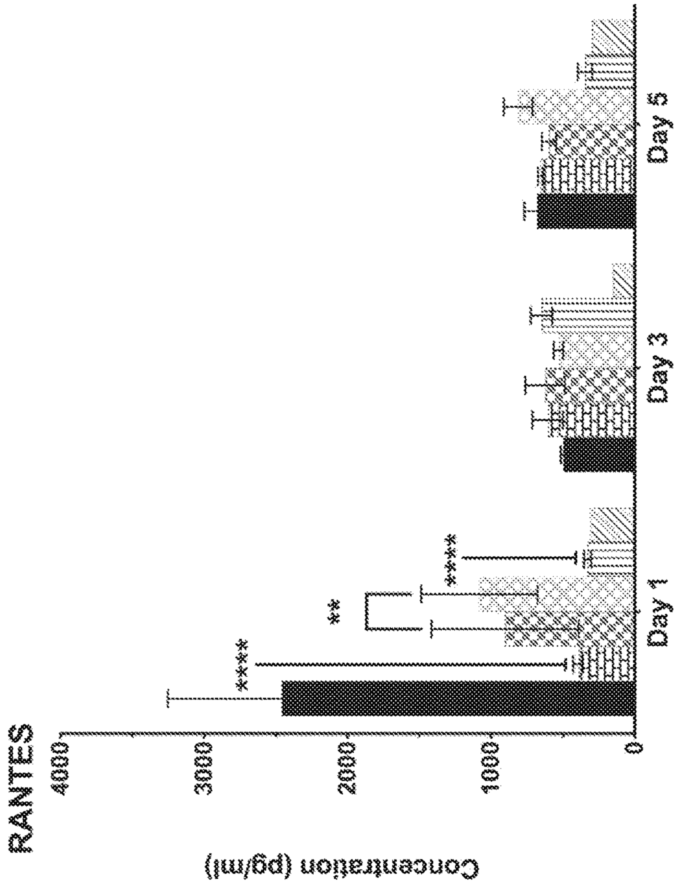
Figure 8C:
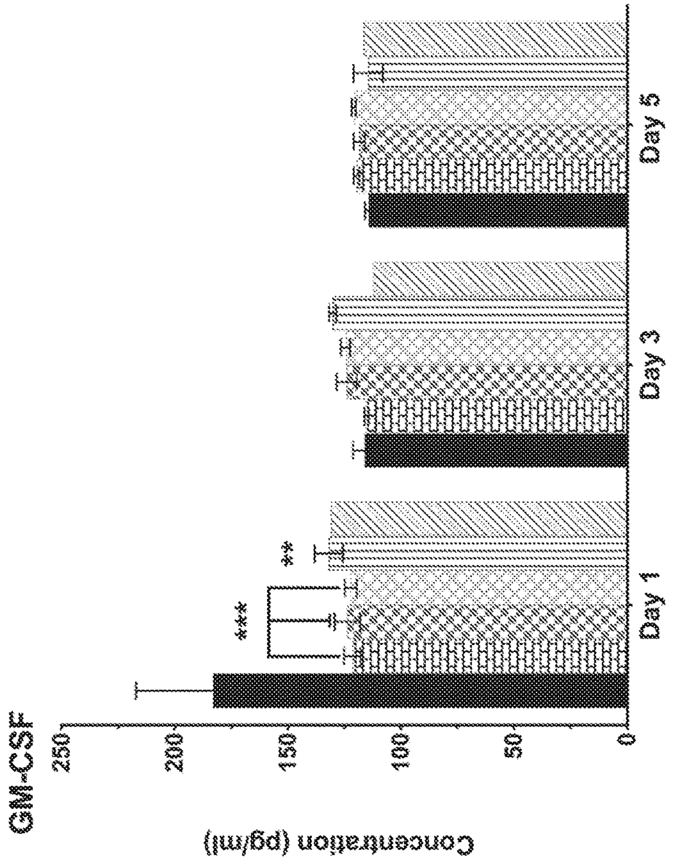

FIGS. 4A-4C shows virus titers in lungs from mice following treatment with compound 8. Lung titers on days 1, 3, and 5 post-infection (p.i.) are shown in FIGS. 4A-4C, respectively. On days 1 and 3 p.i., only the guanidine-treated group showed a reduction in virus titers compared to placebo. See FIGS. 4A and 4B. However, on day 5 p.i., mice treated with the 30 mg dose of compound 8 also showed a reduction in virus titer. See FIG. 4C.

Early activation of the innate immune system helps in the immediate control of a respiratory virus replication and spread (Hsu, Frontiers in Immunology, 2018, 9, 743). Production of antiviral type I interferons, for example, by lung epithelial cells, macrophages, and dendritic cells leads to the expression of IFN-stimulated genes with antiviral and immune-modulatory functions (Iwasaki and Pillai, Nature Reviews Immunology, 2014, 14, 315; Ivashkiv and Donlin, Nature Reviews Immunology, 2014, 14, 36). Production of inflammatory cytokines such as IL-1β, IL-6, and TNF-α is also important in control of respiratory infections.

Cellular immunity was evaluated by quantitation of cytokines and chemokines in lung lavage samples collected on days 1, 3, and 5 p.i. using a multiplex enzyme-linked immunosorbent assay (ELISA). FIGS. 5A-5D show concentrations of IL-1α, IL-1β, IL-2 and IL-3 in lung homogenates from mice following treatment with compound 8 and EV-D68 infection. Treatment with compound 8 at a dose of 30 mg/kg/day increased concentrations of IL-1a (see FIG. 5A) and IL-1β(see FIG. 5B) on day 3 p.i. compared to placebo-treated mice. In addition, the 30 mg treatment also increased IL-3 on day 3 p.i. See FIG. 5B. In addition, all doses of compound 8 decreased IL-3 on day 1. See FIG. 5D.

Concentrations of IL-4, IL-5, IL-6, and IL-10 in lungs from mice following treatment with compound 8 and EV-D68 infection are shown in FIGS. 6A-6D. Treatment with compound 8 at a dose of 100 mg/kg/day increased concentrations of IL-4 (see FIG. 6A), IL-5 (see FIG. 6B), and IL-6 (see FIG. 6C) on day 3 p.i. compared to placebo-treated mice. However, the 100 mg dose also decreased IL-5 on day 1 p.i. See FIG. 6B. In addition, all doses of compound 8 decreased IL-5 on day 1 p.i. (see FIG. 6B), but the 30 mg treatment increased IL-6 on day 3 p.i. See FIGS. 6B and 6C.

FIGS. 7A-7D show concentrations of IL-12p70, IL-17, MCP-1 and IFNγ in lungs from mice following treatment and infection. Treatment with compound 8 at a dose of 100 mg/kg/day decreased concentrations of MCP-1 on day 1 p.i. (see FIG. 7C) and the 10 mg dose decreased IFNγ on day 1 p.i. See FIG. 7D. Other changes included guanidine treatment increasing IL-12p70 on day 3 p.i. (see FIG. 7A) and decreasing MCP-1 (see FIG. 7C) on days 1 and 3 p.i.

Concentrations of TNFα, MIP-1a, GM-CSF, and RANTES in lungs from mice following treatment and infection are shown in FIGS. 8A-8D. Treatment with compound 8 at a dose of 30 mg/kg/day increased concentrations of MIP-1α on day 5 p.i. (see FIG. 8B) and all doses of compound 8 decreased GM-CSF and RANTES on day 1 p.i. See FIGS. 8C and 8D. Other observations included guanidine treatment increasing MIP-1α on day 5 p.i. (see FIG. 8B) and decreasing GM-CSF and RANTES on day 1 p.i. See FIGS. 8C and 8D.

Discussion: The EV-D68 respiratory model based on intranasal infection of 4-week-old AG129 mice is a non-lethal model that includes viremia with rapid tissue distribution of virus, including high virus titers in lung tissues and an elevation of proinflammatory cytokines in the lung. Treatment with all doses of compound 8 reduced blood virus (viremia) on days 1 and 3 post-infection. No virus was detected in the blood of animals treated on day 5 post-infection indicating virus clearance from the blood by that date. In addition, a dose of 30 mg/kg/day reduced lung virus titers on day 5 post-infection compared to placebo-treated mice.

Early activation of the innate immune system can provide more immediate control of a respiratory virus replication and spread (Hsu, Frontiers in Immunology, 2018, 9, 743). Production of antiviral type I interferons, for example, by lung epithelial cells, macrophages, and dendritic cells leads to the expression of IFN-stimulated genes with antiviral and immune-modulatory functions (Iwasaki and Pillai, Nature Reviews Immunology, 2014, 14, 315; Ivashkiv and Donlin, Nature Reviews Immunology, 2014, 14, 36. Production of inflammatory cytokines such as IL-1β, IL-6, and TNF-α is also helpful in control of respiratory infections. Cellular immunity was evaluated by quantitation of cytokines and chemokines in lung lavage samples collected on days 1, 3, and 5 p.i. using a multiplex ELISA.

All doses of compound 8 significantly reduced lung concentrations of IL-3, IL-5, GM-CSF, and RANTES on day 1 after treatment and challenge infection. Additional reductions in cytokine concentrations after treatment and infection included IFNγ and MCP-1 on day 1 for the 10 and 100 mg/kg treatment groups, respectively. An increase in IL-1α, IL-1β, IL-4, and IL-6 were observed on day 3 for the 100 mg/kg treatment groups. In addition, an increase in IL-10 and MIP-1α were observed on day 5 for the 10 and 30 mg/kg treatment groups, respectively.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A compound of the formula (I)

(I)

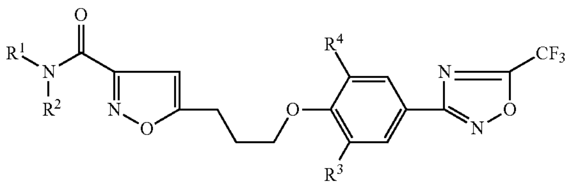

wherein:

$R^1$ and $R^2$ are independently selected from H, a saturated or unsaturated, linear or branched $C_1$-$C_8$alkyl, and benzyl, or wherein $R^1$ and $R^2$ together are C3-Ca alkylene; and $R^3$ and $R^4$ are independently selected from H, fluoro (F), chloro (Cl), methyl (Me), methoxy (OMe), trifluoromethyl ($CF_3$), and nitro ($NO_2$).

2. The compound of claim 1, wherein one or both of $R^3$ and $R^4$ are methyl.

3. The compound of claim 1, wherein one or both of $R^3$ and $R^4$ are fluoro.

4. The compound of claim 1, the compound of Formula (I) is selected from:

N,N-dialkyl-5-(3-{2-methyl-4-[5-(trifluoromethyl)-1,2,4-oxadiazol-3-yl]phenoxy}propyl) isoxazole-3-carboxamide, N,N-dialkyl-5-(3-{2-fluoro-4-[5-(trifluoromethyl)-1,2,4-oxadiazol-3-yl] phenoxy}propyl) isoxazole-3-carboxamide, and N,N-dialkyl-5-(3-{2-nitro-4-[5-(trifluoromethyl)-1,2,4-oxadiazol-3-ylphenoxy}propyl) isoxazole-3-carboxamide.

5. The compound of claim 1, wherein the compound is N,N-dimethyl-5-(3-{2-methyl-4-[5-(trifluoromethyl)-1,2,4-oxadiazol-3-yl] phenoxy}propyl) isoxazole-3-carboxamide.

6. A pharmaceutical composition comprising a compound of claim 1 and a pharmaceutically acceptable carrier.

7. A method of treating or preventing a picornavirus infection in a subject in need thereof, the method comprising administering to the subject an effective amount of a compound of claim 1.

8. The method of claim 7, wherein the subject is an animal.

9. The method of claim 7, wherein the picornavirus infection is a rhinovirus infection or an enterovirus infection.

10. The method of claim 7, wherein the picornavirus infection is a pleconaril-resistant picomavirus infection.

11. The method of claim 7, wherein the compound is N,N-dimethyl-5-(3-{2-methyl-4-[5-(trifluoromethyl)-1,2,4-oxadiazol-3-yl] phenoxy}-propyl) isoxazole-3-carboxamide.

12. The method of claim 7, wherein the method further comprises administering one or more additional therapeutic agents to the subject.

13. A method of treating or preventing an influenza A virus infection in a subject in need thereof, wherein the method comprises administering to the subject a compound of claim 1.

14. A method of treating or preventing a disease or condition caused by a viral infection in a subject in need thereof, wherein the method comprises administering to the subject a compound of claim 1.

15. The method of claim 14, wherein the disease or condition caused by a viral infection is selected from the group consisting of influenza, common cold, aseptic meningitis, encephalitis, hand-foot-and-mouth disease, paralytic poliomyelitis, conjunctivitis, diarrhea, herpetic angina, acute myocarditis, chronic myocarditis, sinusitis, otitis media, and acute flaccid myelitis.

16. The method of claim 14, wherein the compound is N,N-dimethyl-5-(3-{2-methyl-4-[5-(trifluoromethyl)-1,2,4-oxadiazol-3-yl] phenoxy}-propyl) isoxazole-3-carboxamide.

17. The method of claim 8, wherein the subject is a human.

18. The method of claim 12, wherein the one or more additional therapeutic agents comprise an antiviral agent.

19. The method of claim 13, wherein the influenza A virus infection is an influenza A subtype H1N1 virus infection.

20. The method of claim 14, wherein the viral infection is a picornavirus infection or an influenza A viral infection.

* * * * *